US007615632B2

(12) United States Patent
Adin et al.

(10) Patent No.: US 7,615,632 B2
(45) Date of Patent: Nov. 10, 2009

(54) CRYSTALLINE FORMS OF TEMOZOLOMIDE

(75) Inventors: Itai Adin, Beer Sheva (IL); Carmen Iustain, Beer Sheva (IL)

(73) Assignee: Chemagis Ltd., Bnei Brak (IL)

( * ) Notice: Subject to any disclaimer, the term of this patent is extended or adjusted under 35 U.S.C. 154(b) by 447 days.

(21) Appl. No.: 11/024,443

(22) Filed: Dec. 30, 2004

(65) Prior Publication Data
US 2005/0187206 A1    Aug. 25, 2005

Related U.S. Application Data

(60) Provisional application No. 60/532,944, filed on Dec. 30, 2003.

(51) Int. Cl.
*C07D 487/04*   (2006.01)
*A61K 31/4188*  (2006.01)
*A61K 31/53*    (2006.01)
*A61P 35/00*    (2006.01)

(52) U.S. Cl. ............................. 544/179; 514/183
(58) Field of Classification Search ................. 544/179
See application file for complete search history.

(56) References Cited

U.S. PATENT DOCUMENTS

| 5,260,291 | A  | 11/1993 | Lunt et al. |
| 6,844,434 | B2 | 1/2005  | Kuo |
| 6,858,631 | B1 | 2/2005  | Crocker et al. |
| 2002/0095036 | A1 | 7/2002 | Kuo et al. |
| 2004/0223951 | A1 | 11/2004 | Zaknoen |

FOREIGN PATENT DOCUMENTS

| EP | 0262682      | * | 1/1988 |
| FR | 2511679      |   | 2/1983 |
| WO | WO 2005/063757 |   | 7/2005 |

OTHER PUBLICATIONS

Lowe et al. "Antitumor Imidazotetrazines. 25. Crystal Structure of 8-Carbamoyl-3-Methylimidazo[5,1-d]-1,2,3,5-Tetrazin-4(3H)-One (Temozolomide) and Structural Comparisons With the Related Drugs Mitozolomide and DTIC", Journal of Medicinal Chemistry, 35(8): 3377-3382, 1992. Compound 5, Figs.2-3, Table II.
Wang et al. "Preparation and Thermostability of Polymorphs of Temozolomide", Zhongguo Yiyao Gongye Zazhi, 34(4): 178-180, 2003.
Britain et al. "Polymorphism in Pharmaceutical Solids Passage", Polymorphism in Pharmaceutical Solids, p. 235-238, 1999. p. 236, 1. [18-22].
Caira "Crystalline Polymorphism of Organic Compounds", Topics in Current Chemistry, 198: 163-208, 1998. p. 164, §1, p. 165, §2, p. 165, last §—p. 166, §1.
Baig et al. "Antitumour Imidazotetrazines. Part 12. Reactions of Mitozolomide and Its 3-Alkyl Congeners With Oxygen, Nitrogen, Halogen, and Carbon Nucleophiles", J. Chem. Soc. Perkin Trans. I, p. 675-670, 1987.
Brown et al. "Antitumor Imidazotetrazines. 40. Radiosyntheses of [4-11C-Carbonyl]- and [3-N-11C-Methyl]-8-Carbamoyl-3-Methylimidazo[5,1-D]-1,2,3,5-Tetrazin-4(3H)-One (Temozolomide) for Positron Emission Tomography (PET) Studies", Journal of Medicinal Chemistry, 45(25): 5448-5457, 2002.
Clark et al. "Antitumor Imidazotetrazines. 32. Synthesis of Novel Imidazotetrazinones and Related Bicyclic Heterocycles to Probe the Mode of Action of the Antitumor Drug Temozolomide", Journal of Medicinal Chemistry, 38(9): 1493-1504, 1995.
Newlands et al. "Temozolomide: A Review of Its Discovery, Chemical Properties, Pre-Clinical Development and Clinical Trials", Cancer Treatment Reviews, 23: 35-61, 1997.
Stevens et al. "Antitumor Imidazotetrazines. 1. Synthesis and Chemistry of 8-Carbamoyl-3-(2-Chloroethyl)Imidazo[5,1-D]-1,2,3,5-Tetrazin-4(3H)-One, A Novel Broad-Spectrum Antitumor Agent", J. Med. Chem., 27(2): 196-201, 1984.
Wanner et al. "A New Synthesis of Temozolomide", J. Chem. Soc. Perkin Trans. 1, p. 1877-1880, 2002.
Carlton "Microscopy in the Study of Polymorph Stability", Microsc. Microanal., 10(Suppl.2): 1346-1347, 2004.
Haleblian "Characterization of habits and Crystalline Modification of Solids and Their Pharmaceutical Applications", Journal of Pharmaceutical Sciences, 64(8): 1269-1288, Aug. 1975.
Haleblian et al. "Pharmaceutical Applications of Polymorphism", Journal of Pharmaceutical Sciences, 58(8): 911-929, Aug. 1969.
Wang et al. "Alternative Syntheses of the Antitumour Drug Temozolomide Avoiding the Use of Methyl Isocyanate", Journal of the Chemical Society, Chemical Communications, p. 1687-1688, 1994.
European Search Report Dated Sep. 10, 2008 From the European Patent Office Re.: Application No. 04806720.1.
Rodriguez-Hornedo et al. Significance of Controlling Crystallization Mechanisms and Kinetics in Pharmaceutical Systems, Journal of Pharmaceutical Sciences, XP001096590, 88(7): 651-660, Jul. 1, 1999.
Shekunov et al. "Crystallization Processes in Pharmaceutical Technology and Drug Delivery Design", Journal of Crystal Growth, XP004193361, 211(1-4): 122-136, Apr. 1, 2000.
Wang et al., "Antitumor Imidazotetrazines. 35. New Synthetic Routes to the Antitumor Drug Temozolomide", J.Org.Chem, vol. 62, No. 21, pp. 7288-7294 (1997).

* cited by examiner

*Primary Examiner*—Venkataraman Balasubramanian
(74) *Attorney, Agent, or Firm*—Leydig, Voit & Mayer, Ltd.

(57) ABSTRACT

Disclosed are novel crystalline forms of Temozolomide, methods of preparation thereof, medicaments including the novel crystalline forms of Temozolomide, and uses thereof in the treatment of medical conditions.

5 Claims, 20 Drawing Sheets

CRYSTALLINE FORMS OF TEMOZOLOMIDE

This application claims the benefit of priority from U.S. Provisional Patent Application No. 60/532,944, filed Dec. 30, 2003, which is incorporated herein in its entirety.

FIELD AND BACKGROUND OF THE INVENTION

The present invention relates to the field of chemistry and more particularly, to novel crystalline forms of Temozolomide and methods for the preparation thereof. The present invention also relates to the field of pharmacology and more particularly to uses of the novel crystalline forms of Temozolomide in treating medical conditions such as, for example, brain cancer, breast cancer, refractory anaplastic astrocytoma, malignant glioma, glioblastoma multiforme and anaplastic astrocytoma.

Temozolomide is the international non-propriety name used to identify 3-methyl-8-carbamoyl-imidazo[5,1-d]-1,2,3,5-tetrazin-4(3H)-one:

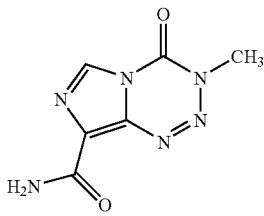

Uses and methods of preparation of Temozolomide are described, for example, in U.S. Pat. No. 5,260,291; U.S. patent application Ser. No. 10/050,768; The Merck Index on CD-ROM, Version 12:3, 1999; Merck & Co. Inc., Whitehouse Station, N.J., USA. Published on CD-ROM by Chapman and Hall/CRC; Stevens et al. *J. Med. Chem.* 1984, 27, 196-201; Baig and Stevens *J. Chem. Soc. Perkin Trans. I* 1987, 675-670; *J. Chem. Soc., Chem. Commun.* 1994, 1687-1688; Clark et al. *J. Med. Chem.* 1995, 38, 1493-1504; Newlands et al. *Cancer Treatment Reviews* 1997 23, 35-61; Brown et al. *J. Med. Chem.* 2002, 45, 5448-5457.

Temozolomide is slightly soluble in water and acidic aqueous solutions (3 mg/ml).

Temozolomide is an antitumor agent indicated for the treatment of patients with malignant glioma such as cancer, brain cancer, breast cancer, refractory anaplastic astrocytoma, malignant glioma, glioblastoma multiforme and anaplastic astrocytoma. Temozolomide is converted in vivo to the cytotoxic monomethyl triazenoimidazole carboxamide.

The presently marketed Temozolomide preparations are hard capsules dosage form containing 5 mg, 20 mg, 100 mg or 250 mg Temozolomide (marketed as Temodar® or Temodal® by Schering Corporation, Kenilworth, N.J., USA).

The crystalline structure of Temozolomide determined by crystallographic methods has not been published in the art. The melting point of Temozolomide has been reported to be 210° C. in Stevens et al. *J. Med. Chem.* 1984, 27, 196-201 and in U.S. Pat. No. 5,260,291. However, in U.S. Pat. No. 5,260,291 is reported that melting was accompanied by " . . . effervescence and darkening from 160° C. to 210° C." indicating that the Temozolomide decomposed rather than melted. It is therefore apparent that melting point is not a property that is useful in characterizing crystals of Temozolomide.

In the Merck index, it is reported that Temozolomide was crystallized from methylene chloride, yielding crystals having a melting point of 212° C.

In U.S. Pat. No. 5,260,291 a number of crystalline forms of Temozolomide were prepared and characterized by infrared spectroscopy in a KBr disk:

a) colorless needles of Temozolomide crystallized from 3:1 v/v mixture of acetone and water (30% by weight water) gave $v_{max}$ at 3410, 3205, 1758, 1730 and 1687 cm$^{-1}$;

b) white microcrystals of Temozolomide crystallized from a 1:3 v/v mixture of acetone and water gave $v_{max}$ at 3430, 3200, 1740 and 1675 cm$^{-1}$; and c) a granular solid of Temozolomide crystallized from hot water gave $v_{max}$ at 3450, 3380, 3200, 1742, 1688 and 1640 cm$^{-1}$.

Two additional crystalline forms of Temozolomide were reported in U.S. Pat. No. 5,260,291 but were not characterized:

d) a light brown microcrystalline Temozolomide crystallized from a reaction solvent comprising methyl isocyanate by the addition of diethyl ether; and e) a pale purple solid Temozolomide crystallized from a reaction solvent comprising dichloromethane and methyl isocyanate by the addition of diethyl ether was dissolved in acetonitrile then recovered by evaporation of the solvent. Although infrared spectroscopy was performed, the results were not reported.

Crystalline forms, that include polymorphs and pseudopolymorphs, are distinct solids sharing the same structural formula, yet having different physical properties due to different conformations and/or orientations of the molecule in the unit cell of the crystal. The physical characteristics, such as solubility and stability, of different crystalline forms are often different and are thus exceptionally relevant in the field of pharmacology.

For a general review of crystalline forms (i.e. polymorphs and pseudopolymorphs) and the pharmaceutical applications of crystalline forms see Wall *Pharm. Manuf.* 1986, 3, 33; Haleblian et al. *J. Pharm. Sci.* 1969, 58, 911; and Haleblian *J. Pharm. Sci.*, 1975, 64, 1269.

Different crystalline forms of a pharmaceutically useful compound provide opportunities to improve the performance characteristics of a pharmaceutical product. Different crystalline forms enlarge the repertoire of materials that a formulation scientist has available for designing, for example, a pharmaceutical dosage form of a drug with a desired release profile, solubility characteristics or other desired characteristic. It is well known that new crystalline forms of known useful compounds are of utility.

There is thus a widely recognized need for, and it would be highly advantageous to have new and distinct crystalline forms of Temozolomide.

SUMMARY OF THE INVENTION

The present invention successfully addresses the widely recognized need for new crystalline forms of Temozolomide by providing nine novel crystalline forms of Temozolomide.

According to the teachings of the present invention there is provided a crystalline Temozolomide Form I comprising at least one of the characteristics selected from the group consisting of a powder X-ray diffraction pattern exhibiting peaks at diffraction angles 2θ of about 10.8, 11.3 and 19.1±0.2°; and an infrared spectrum with $v_{max}$ at about 3451, 1749 and 1736±4 cm$^{-1}$.

In an embodiment of the crystalline Temozolomide Form I of the present invention the characterizing peaks of the powder X-ray diffraction pattern are of a relative intensity of at least about 20%.

In an embodiment of the crystalline Temozolomide Form I of the present invention, the powder X-ray diffraction pattern further exhibits peaks 2θ at diffraction angles of about 17.7 and 29.0±0.2°.

In an embodiment of the crystalline Temozolomide Form I of the present invention, the infrared spectrum has $v_{max}$ also at about 3140 and 1585±4 cm$^{-1}$.

The powder X-ray diffraction pattern of an embodiment of the crystalline Temozolomide Form I of the present invention is substantially as depicted in FIG. 1.

The infrared spectrum of an embodiment of the crystalline Temozolomide Form I of the present invention is substantially as depicted in FIG. 2.

According to the teachings of the present invention there is also provided a process of preparing crystalline Temozolomide Form I, the process comprising contacting Temozolomide with a solvent, the solvent including pyridine as a solvent component, to thereby form a Temozolomide solution; crystallizing the Temozolomide in the solution, to thereby obtain the crystalline Temozolomide Form I; and isolating the crystalline Temozolomide Form I.

In an embodiment of the present invention, the solvent component further comprises isopropanol. In an embodiment of the present invention, the ratio between the pyridine and the isopropanol is about 8 volumes isopropanol to 15 volumes pyridine.

According to the teachings of the present invention there is also provided a crystalline Temozolomide Form II comprising at least one of the characteristics selected from the group consisting of a) a powder X-ray diffraction pattern exhibiting peaks at diffraction angles 2θ of about 10.8, 11.3, 14.5, 16.0, 17.9 and 19.1±0.2°; and an infrared spectrum with $v_{max}$ about 3451, 1749 and 1736±4 cm$^{-1}$.

In an embodiment of the crystalline Temozolomide Form II of the present invention the characterizing peaks of the powder X-ray diffraction pattern are of a relative intensity of at least about 20%.

In an embodiment of the crystalline Temozolomide Form II of the present invention, the powder X-ray diffraction pattern further exhibits peaks at diffraction angles 2θ of about 17.7 and 29.0±0.2°.

In an embodiment of the crystalline Temozolomide Form II of the present invention, the infrared spectrum has $v_{max}$ also at about 3140 and 1585±4 cm$^{-1}$.

The powder X-ray diffraction pattern of an embodiment of the crystalline Temozolomide Form II of the present invention is substantially as depicted in FIG. 3.

The infrared spectrum of an embodiment of the crystalline Temozolomide Form II of the present invention is substantially as depicted in FIG. 4.

According to the teachings of the present invention there is also provided a process of preparing crystalline Temozolomide Form II, the process comprising contacting Temozolomide with a solvent, the solvent including pyridine as a solvent component, to thereby form a Temozolomide solution; crystallizing the Temozolomide in the solution, to thereby obtain the crystalline Temozolomide; isolating the crystalline Temozolomide, and drying the crystalline Temozolomide at a reduced pressure, to thereby obtain the Temozolomide Form II. In an embodiment of the present invention, the solvent component further comprises isopropanol. In an embodiment of the present invention, the ratio between the pyridine and the isopropanol is about 8 volumes isopropanol to 15 volumes pyridine.

According to the teachings of the present invention there is also provided a process of preparing crystalline Temozolomide Form II the process comprising providing crystalline Temozolomide Form I, preferably as described hereinabove, and heating the crystalline Temozolomide Form I to a transubstantiation temperature of about 30° C. and under reduced pressure to thereby obtain the crystalline Temozolomide Form II.

According to the teachings of the present invention there is also provided a crystalline Temozolomide Form III comprising at least one of the characteristics selected from the group consisting of a) a powder X-ray diffraction pattern exhibiting peaks at diffraction angles 2θ of about 10.8, 14.7 and 26.6±0.2°; and an infrared spectrum with $v_{max}$ at about 1678, 731 and 712±4 cm$^{-1}$.

In an embodiment of the crystalline Temozolomide Form III of the present invention the characterizing peaks of the powder X-ray diffraction pattern are of a relative intensity of at least about 20%.

In an embodiment of the crystalline Temozolomide Form III of the present invention, the powder X-ray diffraction pattern further exhibits peaks at diffraction angles 2θ of about 28.8 and 19.7±0.2°.

The powder X-ray diffraction pattern of an embodiment of the crystalline Temozolomide Form III of the present invention is substantially as depicted in FIG. 6.

The infrared spectrum of an embodiment of the crystalline Temozolomide Form III of the present invention is substantially as depicted in FIG. 7.

According to the teachings of the present invention there is also provided a process of preparing crystalline Temozolomide Form III, the process comprising contacting Temozolomide with a solvent, the solvent including at least one solvent component selected from the group consisting of dimethylformamide, ethanol, and a mixture of benzyl alcohol and isopropanol, to thereby form a Temozolomide solution; crystallizing the Temozolomide in the solution, to thereby obtain the crystalline Temozolomide Form III; and isolating the crystalline Temozolomide Form III.

In an embodiment of the present invention, the solvent component is dimethylformamide.

In an embodiment of the present invention, the solvent component is ethanol and the crystallizing includes allowing the Temozolomide solution to cool down to a temperature lower than or equal to about 5° C.

In an embodiment of the present invention, the solvent component comprises benzyl alcohol and isopropanol.

In this embodiment of the present invention contacting the Temozolomide with the solvent includes dissolving the Temozolomide in a solvent including benzyl alcohol and crystallizing includes adding the isopropanol to the Temozolomide solution. In an embodiment of the present invention the isopropanol is added to the Temozolomide solution at a temperature of about 90° C. In an embodiment of the present invention, subsequent to adding the isopropanol, the crystalline Temozolomide Form III is allowed to cool down to a temperature lower than or equal to about 25° C.

According to the teachings of the present invention there is also provided a process of preparing crystalline Temozolomide Form III, the process comprising providing crystalline Temozolomide Form II, preferably as described hereinabove, heating the crystalline Temozolomide Form II to a transubstantiation temperature of about 120° C. to thereby obtain the crystalline Temozolomide Form III.

According to the teachings of the present invention there is also provided a crystalline Temozolomide Form IV comprising at least one of the characteristics selected from the group consisting of a) a powder X-ray diffraction pattern exhibiting peaks at diffraction angles 2θ of about 4.2 and 12.6±0.2°; and an infrared spectrum with $v_{max}$ at about 3387,1759 and 1734±4 cm$^{-1}$.

In an embodiment of the crystalline Temozolomide Form IV of the present invention the characterizing peaks of the powder X-ray diffraction pattern are of a relative intensity of at least about 20%.

In an embodiment of the crystalline Temozolomide Form IV of the present invention, the powder X-ray diffraction pattern further exhibits peaks at diffraction angles 2θ of about 14.8 and 16.7±0.2°.

In an embodiment of the crystalline Temozolomide Form IV of the present invention, the infrared spectrum has $v_{max}$ also at about 1009±4 cm$^{-1}$.

The powder X-ray diffraction pattern of an embodiment of the crystalline Temozolomide Form IV of the present invention is substantially as depicted in FIG. 8.

The infrared spectrum of an embodiment of the crystalline Temozolomide Form IV of the present invention is substantially as depicted in FIG. 9.

According to the teachings of the present invention there is also provided a process of preparing crystalline Temozolomide Form IV, the process comprising contacting Temozolomide with a solvent, the solvent including benzyl alcohol as a solvent component, to thereby form a Temozolomide solution; crystallizing the Temozolomide in the solution, to thereby obtain the crystalline Temozolomide Form IV; and isolating the crystalline Temozolomide Form IV.

According to the teachings of the present invention there is also provided a crystalline Temozolomide Form V comprising at least one of the characteristics selected from the group consisting of a) a powder X-ray diffraction pattern exhibiting peaks at diffraction angles 2θ of about 11.4, 13.2, 21.5, 26.5 and 26.8±0.2°; and an infrared spectrum with $v_{max}$ at about 3113, 1755 and 1619±4 cm$^{-1}$.

In an embodiment of the crystalline Temozolomide Form V of the present invention the characterizing peaks of the powder X-ray diffraction pattern are of a relative intensity of at least about 20%.

In an embodiment of the crystalline Temozolomide Form V of the present invention, the powder X-ray diffraction pattern further exhibits peaks at diffraction angles 2θ of about 30.9±0.2°.

In an embodiment of the crystalline Temozolomide Form V of the present invention, the infrared spectrum has $v_{max}$ also at about 1682 and 1356±4 cm$^{-1}$.

The powder X-ray diffraction pattern of an embodiment of the crystalline Temozolomide Form V of the present invention is substantially as depicted in FIG. 10.

The infrared spectrum of an embodiment of the crystalline Temozolomide Form V of the present invention is substantially as depicted in FIG. 11.

According to the teachings of the present invention there is also provided a process of preparing crystalline Temozolomide Form V the process comprising contacting Temozolomide with a solvent, the solvent including ethylene glycol as a solvent component, to thereby form a Temozolomide solution; crystallizing the Temozolomide in the solution, to thereby obtain the crystalline Temozolomide Form V and isolating the crystalline Temozolomide Form V.

According to the teachings of the present invention there is also provided a crystalline Temozolomide Form VI comprising at least one of the characteristics selected from the group consisting of a) a powder X-ray diffraction pattern exhibiting peaks at diffraction angles 2θ of about 8.4, 14.4 and 25.1±0.2°; and an infrared spectrum with $v_{max}$ at about 3336, 3276, 1606 and 877±4 cm$^{-1}$.

In an embodiment of the crystalline Temozolomide Form VI of the present invention the characterizing peaks of the powder X-ray diffraction pattern are of a relative intensity of at least about 20%.

In an embodiment of the crystalline Temozolomide Form VI of the present invention, the infrared spectrum has $v_{max}$ also at about 3126, 1741 and 802±4 cm$^{-1}$.

The powder X-ray diffraction pattern of an embodiment of the crystalline Temozolomide Form VI of the present invention is substantially as depicted in FIG. 12.

The infrared spectrum of an embodiment of the crystalline Temozolomide Form VI of the present invention is substantially as depicted in FIG. 13.

According to the teachings of the present invention there is also provided a process of preparing crystalline Temozolomide Form VI the process comprising contacting Temozolomide with a solvent, the solvent including nitroethane as a solvent component, to thereby form a Temozolomide solution; crystallizing the Temozolomide in the solution, to thereby obtain the crystalline Temozolomide Form VI and isolating the crystalline Temozolomide Form VI.

According to the teachings of the present invention there is also provided a crystalline Temozolomide Form VII comprising at least one of the characteristics selected from the group consisting of a) a powder X-ray diffraction pattern exhibiting peaks at diffraction angles 2θ of about 7.4 and 14.7±0.2°; and an infrared spectrum with $v_{max}$ at about 3115, 1732, 1605 and 1566±4 cm$^{-1}$.

In an embodiment of the crystalline Temozolomide Form VII of the present invention the characterizing peaks of the powder X-ray diffraction pattern are of a relative intensity of at least about 20%.

In an embodiment of the crystalline Temozolomide Form VII of the present invention, the powder X-ray diffraction pattern further exhibits peaks at diffraction angles 2θ of about 14.1 and 28.2±0.2°.

In an embodiment of the crystalline Temozolomide Form VII of the present invention, the powder X-ray diffraction pattern further exhibits peaks at diffraction angles 2θ of about 22.2, 23.0 and 23.9±0.2°.

In an embodiment of the crystalline Temozolomide Form VII of the present invention, the infrared spectrum has $v_{max}$ also at about 1263±4 cm$^{-1}$.

The powder X-ray diffraction pattern of an embodiment of the crystalline Temozolomide Form VII of the present invention is substantially as depicted in FIG. 15.

The infrared spectrum of an embodiment of the crystalline Temozolomide Form VII of the present invention is substantially as depicted in FIG. 16.

According to the teachings of the present invention there is also provided a process of preparing crystalline Temozolomide Form VII the process comprising contacting Temozolomide with a solvent, the solvent including dimethylsulfoxide as a solvent component, to thereby form a Temozolomide solution; crystallizing the Temozolomide in the solution, to thereby obtain the crystalline Temozolomide Form VII and isolating the crystalline Temozolomide Form VII.

In an embodiment of the present invention, crystallizing includes allowing the Temozolomide solution to cool down to a temperature of about 5° C.

According to the teachings of the present invention there is also provided a crystalline Temozolomide Form VIII comprising at least one of the characteristics selected from the group consisting of a) a powder X-ray diffraction pattern exhibiting peaks at diffraction angles 2θ of about 9.3, 10.8, 11.8, 14.7, 26.6 and 28.2±0.2°; and an infrared spectrum with $v_{max}$ at about 1678, 731 and 712±4 cm$^{-1}$.

In an embodiment of the crystalline Temozolomide Form VIII of the present invention the characterizing peaks of the powder X-ray diffraction pattern are of a relative intensity of at least about 20%.

In an embodiment of the crystalline Temozolomide Form VIII of the present invention, the powder X-ray diffraction pattern further exhibits peaks at diffraction angles 2θ of about 28.8 and 19.7±0.2°.

The powder X-ray diffraction pattern of an embodiment of the crystalline Temozolomide Form VIII of the present invention is substantially as depicted in FIG. 17.

The infrared spectrum of an embodiment of the crystalline Temozolomide Form VIII of the present invention is substantially as depicted in FIG. 18.

According to the teachings of the present invention there is also provided a process of preparing crystalline Temozolomide Form VIII the process comprising contacting Temozolomide with a solvent, the solvent including a solvent component selected from the group consisting of acetone, dichloromethane or a mixture thereof, to thereby form a Temozolomide solution; crystallizing the Temozolomide in the solution, to thereby obtain the crystalline Temozolomide Form VIII and isolating the crystalline Temozolomide Form VIII wherein if a solvent component includes acetone then the solvent includes less than 5% by weight water.

According to the teachings of the present invention there is also provided a crystalline Temozolomide Form IX comprising at least one of the characteristics selected from the group consisting of a) a powder X-ray diffraction pattern exhibiting peaks at diffraction angles 2θ of about 13.7, 16.1, 23.2 and 30.1±0.2°; and an infrared spectrum with $v_{max}$ at about 3439, 3122, 1741 and 1271±4 cm$^{-1}$.

In an embodiment of the crystalline Temozolomide Form IX of the present invention the characterizing peaks of the powder X-ray diffraction pattern are of a relative intensity of at least about 20%.

In an embodiment of the crystalline Temozolomide Form IX of the present invention, the powder X-ray diffraction pattern further exhibits peaks at diffraction angles 2θ of about 26.4±0.2°.

In an embodiment of the crystalline Temozolomide Form IX of the present invention, the powder X-ray diffraction pattern further exhibits peaks at diffraction angles 2θ of about 17.5 and 19.9±0.2°.

The powder X-ray diffraction pattern of an embodiment of the crystalline Temozolomide Form IX of the present invention is substantially as depicted in FIG. 19.

The infrared spectrum of an embodiment of the crystalline Temozolomide Form IX of the present invention is substantially as depicted in FIG. 20.

According to the teachings of the present invention there is also provided a process of preparing crystalline Temozolomide Form IX the process comprising providing crystalline Temozolomide Form VI, heating the crystalline Temozolomide Form VI to a transubstantiation temperature of about 120° C., to thereby obtain the crystalline Temozolomide Form IX.

In an embodiment of the present invention, providing the Temozolomide Form VI is as described hereinabove.

In all the processes described hereinabove contacting the Temozolomide with the solvent includes dissolving the Temozolomide in the solvent at elevated temperatures, as is exemplified in the Examples section that follows. The crystallizing includes allowing the Temozolomide solution to cool down to a temperature lower than or equal to about 25° C. The isolating comprises separating, preferably by filtering, the crystalline Temozolomide from the solution.

The various crystalline Temozolomide Forms are preferably dried subsequent to separating from the solution. The drying is effected at room temperature and in some cases, as indicated in the Examples section that follows, the drying is effected at a reduced pressure less than or equal to about 100 mm Hg.

According to the teachings of the present invention there is also provided a pharmaceutical composition comprising at least one crystalline Temozolomide selected from the group consisting of Temozolomide Form I, Temozolomide Form II, Temozolomide Form III, Temozolomide Form IV, Temozolomide Form V, Temozolomide Form VI, Temozolomide Form VII, Temozolomide Form VIII and Form Temozolomide IX; and a pharmaceutically acceptable carrier.

According to the teachings of the present invention there is also provided a method of producing a Temozolomide-containing medicament comprising: providing at least one Temozolomide-containing component selected from the group consisting of Temozolomide Form I, Temozolomide Form II, Temozolomide Form III, Temozolomide Form IV, Temozolomide Form V, Temozolomide Form VI, Temozolomide Form VII, Temozolomide Form VIII, and Temozolomide Form IX; and combining the at least one Temozolomide-containing component with a pharmaceutically acceptable carrier.

According to the teachings of the present invention there is also provided a method of treatment comprising administering a pharmaceutically effective amount of Temozolomide to a mammal (preferably a human) in need thereof, wherein the Temozolomide includes at least one crystalline Temozolomide selected from the group consisting of Temozolomide Form I, Temozolomide Form II, Temozolomide Form III, Temozolomide Form IV, Temozolomide Form V, Temozolomide Form VI, Temozolomide Form VII, Temozolomide Form VIII and Temozolomide Form IX.

In an embodiment of the present invention the need arises from a medical condition selected from the group consisting of cancer, brain cancer, breast cancer, refractory anaplastic astrocytoma, malignant glioma, glioblastoma multiforme and anaplastic astrocytoma.

The present invention successfully addresses the shortcomings of the presently known configurations by providing novel Temozolomide polymorphs.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
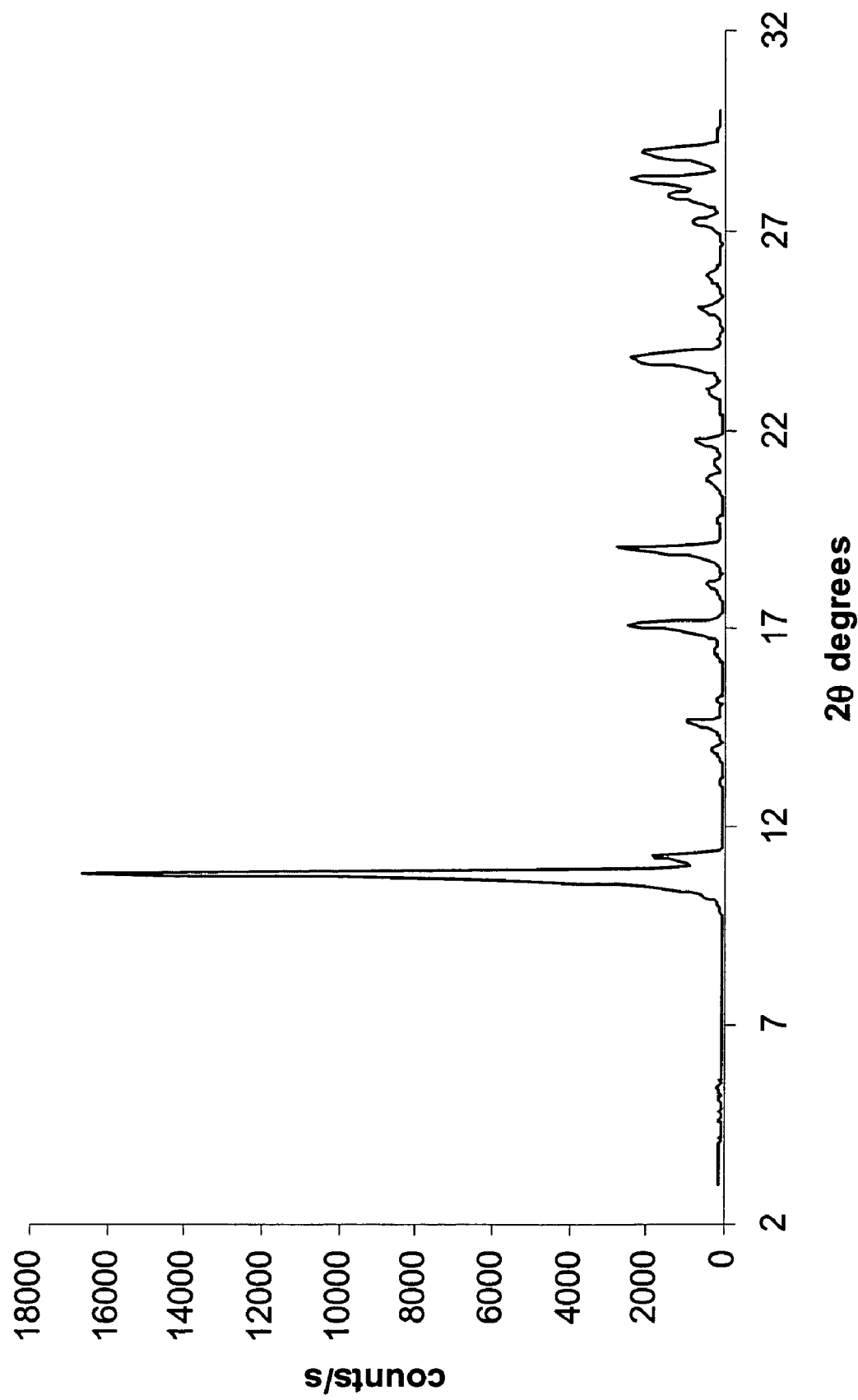
FIG. 1 presents an X-ray powder diffractogram of Temozolomide Form I.

The present invention is of novel crystalline forms of Temozolomide, preparation thereof and uses thereof in the manufacture of medicaments for and in treatment of medical conditions such as, but not limited to cancer, brain cancer, breast cancer, refractory anaplastic astrocytoma, malignant glioma, glioblastoma multiforme and anaplastic astrocytoma.

The principles, uses and implementations of the teachings of the present invention may be better understood with reference to the accompanying description and figures. Upon perusal of the description and figures present herein, one skilled in the art is able to implement the teachings of the present invention without undue effort or experimentation.

Before explaining at least one embodiment of the invention in detail, it is to be understood that the invention is not limited in its application to the details set forth herein. The invention can be implemented with other embodiments and can be practiced or carried out in various ways. It is also understood that the phraseology and terminology employed herein is for descriptive purpose and should not be regarded as limiting.

Generally, the nomenclature used herein and the laboratory procedures utilized in the present invention include techniques from the fields of analytical chemistry, biology, chemistry, engineering and synthetic chemistry. Such techniques are thoroughly explained in the literature. Unless otherwise defined, all technical and scientific terms used herein have the same meaning as commonly understood by one of ordinary skill in the art to which the invention belongs. In addition, the descriptions, materials, methods and examples are illustrative only and not intended to be limiting. Methods and materials similar or equivalent to those described herein can be used in the practice or testing of the present invention. All publications, patent applications, patents and other references mentioned are incorporated by reference in their entirety as if fully set forth herein. In case of conflict, the specification herein, including definitions, will control.

As used herein, the terms "comprising" and "including" or grammatical variants thereof are to be taken as specifying the stated features, integers, steps- or components but do not preclude the addition of one or more additional features, integers, steps, components or groups thereof. These terms encompass the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

The terms "method" and "process" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts. Implementation of the methods of the present invention involves performing or completing selected tasks or steps manually, automatically, or a combination thereof.

General techniques for the crystallization of compounds are known to those skilled in the art. Such techniques include crystallization from solvents, thermal treatment and sublimation. It is not possible to know, a priori and without extensive experimentation, which procedure, process or regime will provide good crystallization of a given compound. Further, it is not known how many different crystalline forms a given compound may have.

The nine novel crystalline forms of the present invention disclosed herein, referred to herein as Temozolomide Forms I-IX, as well as the methods of preparing these nine crystalline forms have not been described nor suggested hitherto.

The Temozolomide crystalline forms of the present invention may contain unnatural proportions of atomic isotopes at one or more of the atoms that constitute such compounds. For example, the Temozolomide may be radiolabeled with radioactive isotopes, such as for example tritium ($^3$H) or carbon-14 ($^{14}$C). All isotopic variations of the compounds of the present invention, whether radioactive or not, are intended to be encompassed within the scope of the present invention.

Generally, the crystalline forms of the present invention are prepared by contacting Temozolomide with a solvent, the solvent including at least one particular solvent component. One preferred method of contacting Temozolomide with a solvent is by dissolving the Temozolomide in the solvent (generally at elevated temperatures) and then crystallizing the dissolved Temozolomide from the solvent using conventional techniques (e.g., slow or fast cooling, addition of a crystallization solvent, drying at atmospheric or reduced pressure), so as to form the desired crystalline form of Temozolomide. The type of crystal form that is produced may further be influenced by the conditions of the crystallization.

In certain embodiments, crystalline forms of the present invention are prepared using a process that does not necessarily include contacting Temozolomide with a solvent. For example, as is detailed below, Temozolomide Form III can optionally be prepared by heating Temozolomide Form II and Temozolomide Form IX is prepared by heating Temozolomide Form VI.

The solvent components used in producing the crystalline forms of the present invention include pyridine, a mixture of pyridine and isopropanol, dimethylformamide, ethanol, benzyl alcohol, benzyl alcohol together with, acetone, methylene chloride, ethylene glycol, nitroethane and dimethylsulfoxide. The nature of the particular solvent component determines which of the crystalline forms is produced. Generally a solvent includes at least 50% by weight of an appropriate solvent component, preferably at least 70% by weight of the solvent component, more preferably at least 80% by weight of the solvent component, more preferably at least 90% by weight of the solvent component or even substantially consists of the solvent component.

The novel crystalline forms of the present invention, Temozolomide Forms I-IX, have been characterized by powder X-ray diffraction, infrared absorption spectrometry and differential scanning calorimetry (DSC), as is detailed hereinunder.

Temozolomide Form I and Temozolomide Form II

Temozolomide Form I is prepared by contacting Temozolomide with a solvent including pyridine or a pyridine-isopropanol mixture as a solvent component, followed by slow or rapid cooling. Temozolomide Form II is prepared by crystallization of Temozolomide from a solvent including pyridine or a pyridine-isopropanol mixture as a solvent component, followed by vacuum (reduced pressure) drying (e.g., less than about 100 mm Hg), preferably while heating (e.g., above 25° C.). Temozolomide Form II can also be prepared by heating Temozolomide Form I to a temperature of about 30° C. under conditions of reduced pressure (i.e., equal to or less than 100 mm Hg).

When the solvent component is a pyridine-isopropanol mixture, a suitable ratio is about 8 volumes isopropanol to 15 volumes pyridine.

Figure 3:
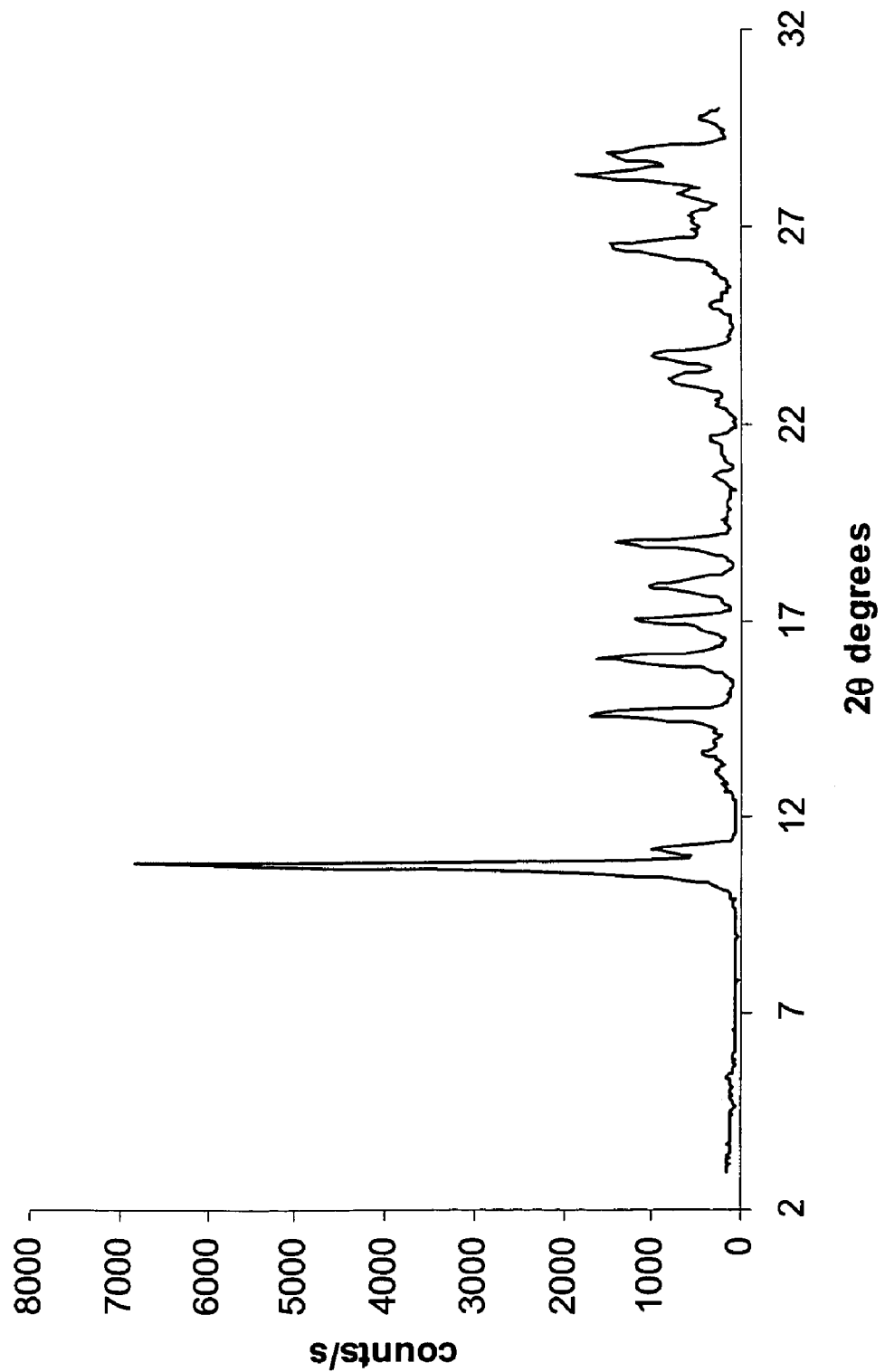
FIG. 3 presents an X-ray powder diffractogram of Temozolomide Form II.

The powder X-ray diffraction pattern of Temozolomide Form I (set forth in Table 1 below and further presented in FIG. 1) and of Temozolomide Form II (set forth Table 2 below and further resented in FIG. 3) show a certain similarity with reflections characteristic for both Form I and Form II at about 10.8, 11.3 and 19.1±0.2°2θ and additional characteristic reflections at about 17.7 and 29.0±0.2°2θ. Temozolomide Form II shows unique reflections at about 14.5, 16.0 and 17.9±0.2°2θ.

Figure 2:
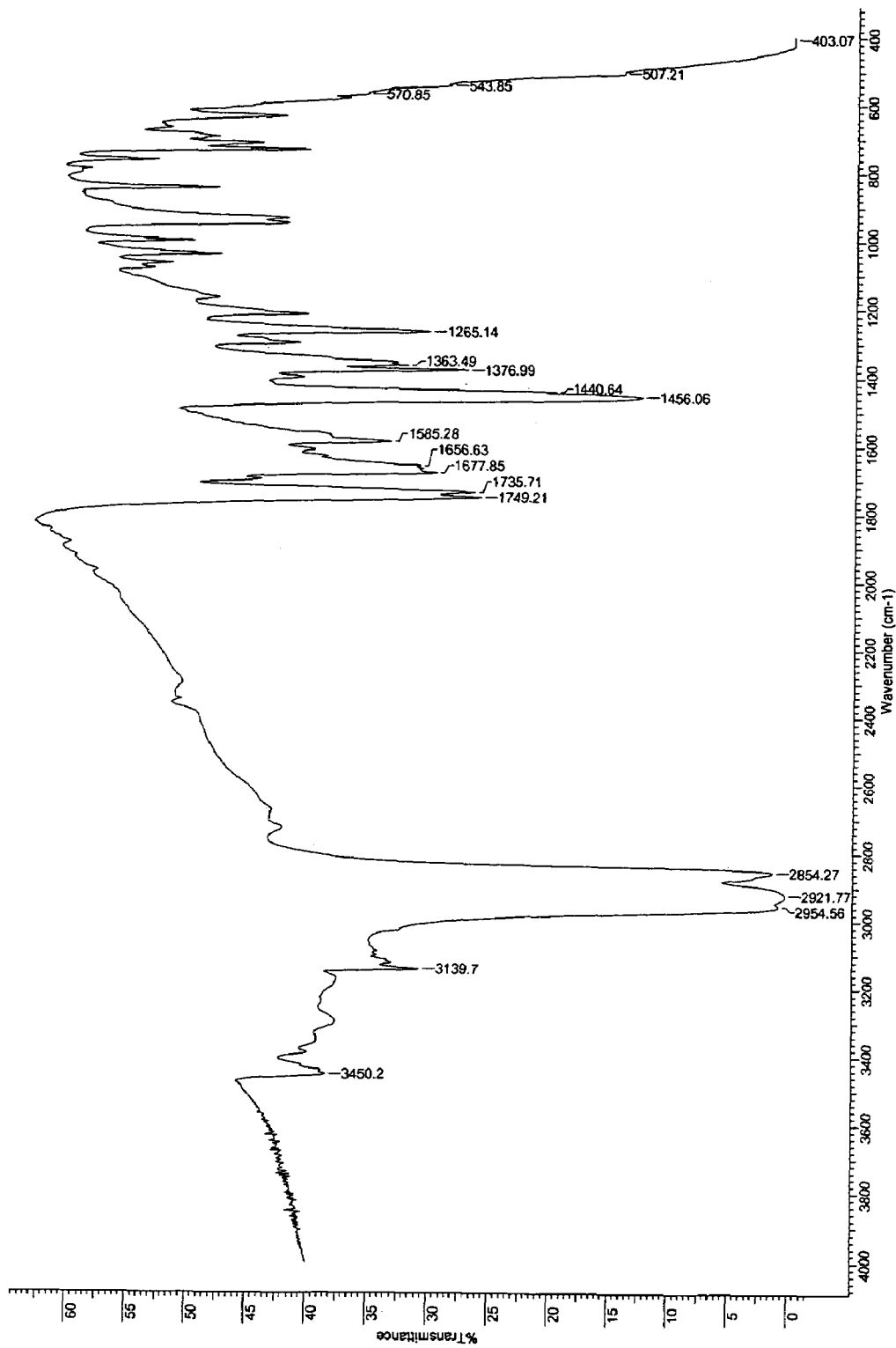
FIG. 2 presents an infrared spectrum of Temozolomide Form I.
Figure 4:
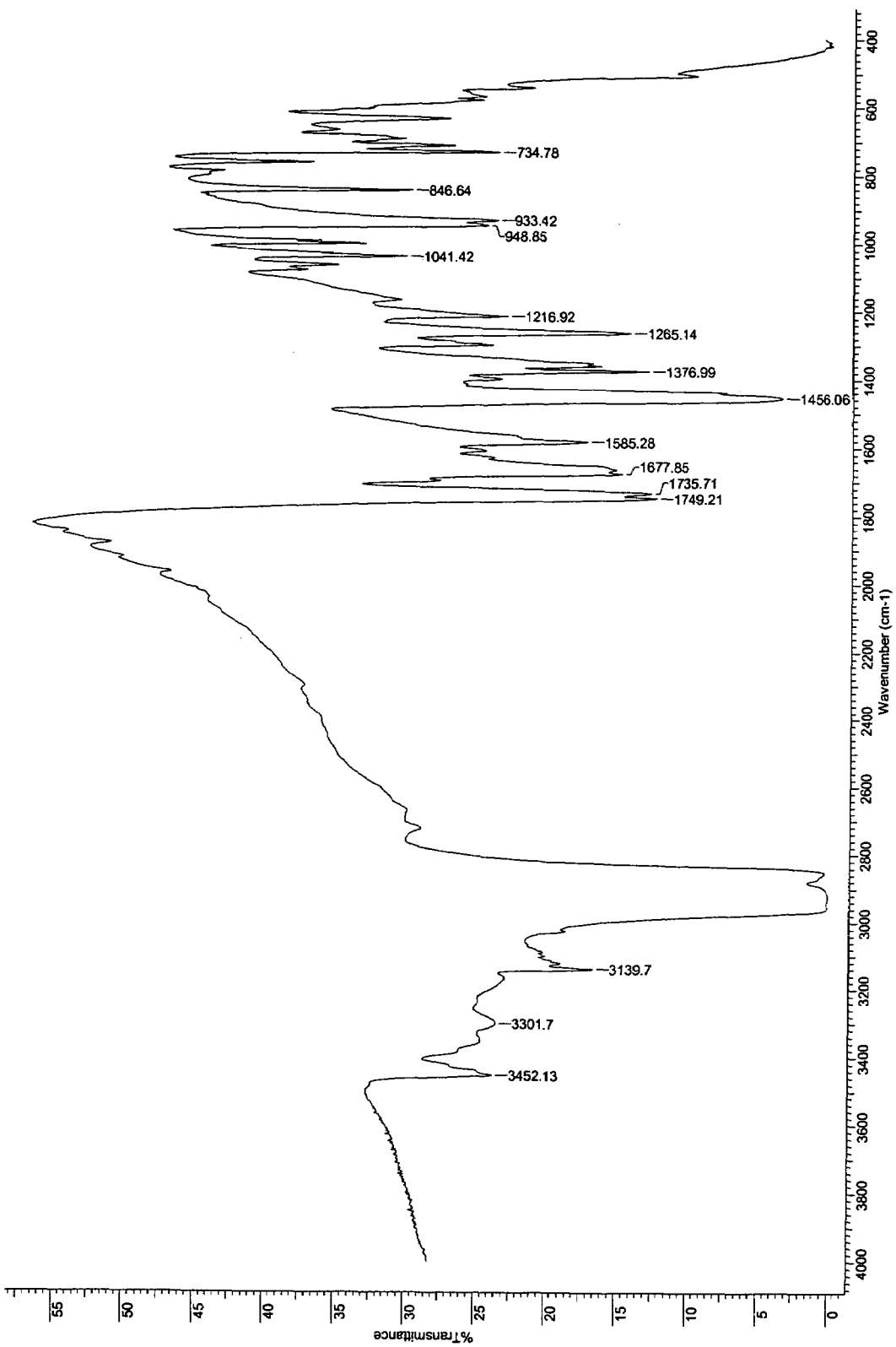
FIG. 4 presents an infrared spectrum of Temozolomide Form II.

The infrared absorption spectra of Temozolomide Form I and Form II are presented in FIG. 2 and FIG. 4, respectively. Characteristic absorption peaks for both forms are found at about 3451, 1749 and 1736±4 cm$^{-1}$ and additional characteristic absorption peaks of both Form I and II are found at about 3140 and 1585±4 cm$^{-1}$.

The DSC curve of Temozolomide Form I exhibits only one broad exothermic peak around 200° C. (data not shown), corresponding to decomposition.

It is assumed that upon heating Temozolomide Form I (at 30° C.) in vacuum, Form I undergoes a solid-solid transition to Temozolomide Form II. When Form I is studied using DSC, no noteworthy behavior except decomposition (vide supra) is observed such as an exothermic or endothermic transition of Form I to Form II. The fact that the transition of Form I to Form II is not detected by DSC at temperatures below the decomposition temperature of Temozolomide indicates that the transition is vacuum-mediated.

As is discussed above, the differences between Temozolomide Form I and Temozolomide Form II are clear. While Temozolomide Form I is prepared by contacting Temozolomide with a solvent including pyridine or a pyridine-isopropanol mixture as a solvent component, followed by slow or rapid cooling, Temozolomide Form II is prepared by crystallization of Temozolomide from a solvent including pyridine or a pyridine-isopropanol mixture as a solvent component, followed by vacuum drying. Temozolomide Form II can also be prepared by heating Temozolomide Form I. Further, it is seen that the powder X-ray diffraction pattern of Temozolomide From II shows reflections at about 14.5, 16.0 and 17.9±0.2°2θ which are not shown in the powder X-ray diffraction pattern of Temozolomide Form I.

Figure 5:
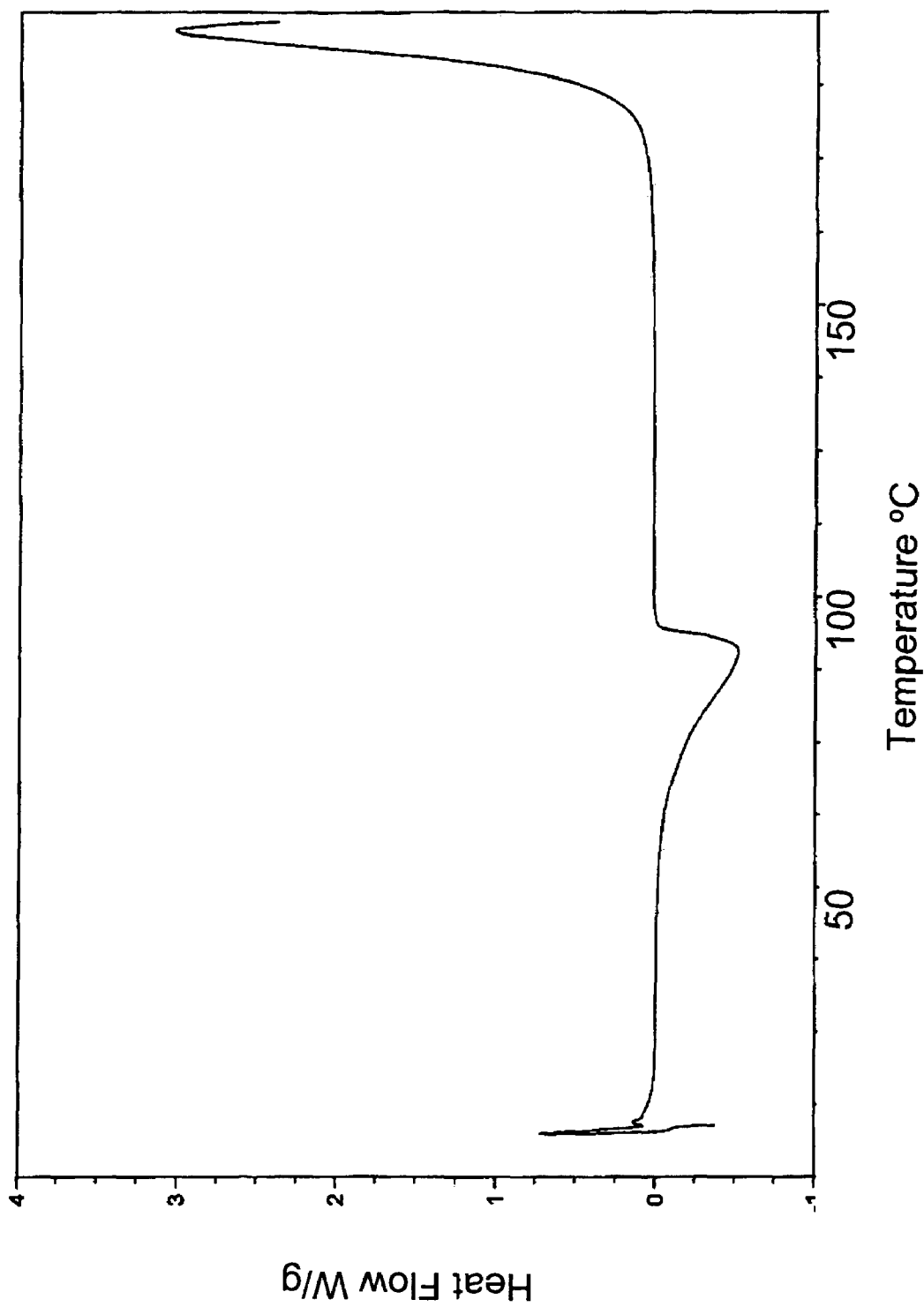
FIG. 5 presents a differential scanning calorimetry curve of Temozolomide Form II.

Upon heating to a temperature of about 120° C., Temozolomide Form II undergoes a solid-solid transition to Temozolomide Form III, vide infra. This transition is seen as an endothermic peak in the DSC curve of Temozolomide Form II (as shown in FIG. 5).

TABLE 1

Form I - Powder X-ray diffraction reflection positions and intensities

| Rel. Intensity (%) | reflection (±0.2 °2θ) |
| --- | --- |
| 5 | 5.4 |
| 100 | 10.8 |
| 29 | 11.3 |
| 4 | 13.1 |
| 9 | 14.0 |
| 20 | 14.7 |
| 5 | 15.2 |
| 9 | 16.5 |
| 36 | 17.1 |
| 13 | 18.2 |
| 38 | 19.1 |
| 7 | 19.8 |
| 13 | 20.8 |
| 8 | 21.2 |
| 17 | 21.7 |
| 11 | 22.6 |
| 12 | 23.0 |
| 29 | 23.7 |
| 29 | 23.9 |
| 10 | 24.4 |
| 13 | 25.1 |
| 18 | 25.9 |
| 15 | 27.2 |
| 23 | 27.9 |
| 32 | 28.3 |
| 38 | 29.0 |
| 15 | 30.3 |

TABLE 2

Form II - Powder X-ray diffraction reflection positions and intensities

| Rel. Intensity (%) | reflection (±0.2 °2θ) |
|---|---|
| 100 | 10.8 |
| 36 | 11.2 |
| 11 | 12.8 |
| 18 | 13.1 |
| 22 | 13.7 |
| 17 | 14.0 |
| 24 | 14.5 |
| 18 | 14.9 |
| 18 | 15.2 |
| 57 | 16.0 |
| 26 | 16.4 |
| 48 | 17.1 |
| 30 | 17.9 |
| 17 | 18.2 |
| 26 | 19.0 |
| 5 | 20.1 |
| 14 | 20.7 |
| 6.0 | 21.1 |
| 13 | 21.7 |
| 14 | 22.6 |
| 29 | 23.0 |
| 34 | 23.2 |
| 45 | 23.7 |
| 12 | 25.0 |
| 20 | 25.8 |
| 22 | 26.9 |
| 23 | 27.3 |
| 37 | 27.8 |
| 66 | 28.3 |
| 36 | 28.9 |
| 23 | 30.2 |

Temozolomide Form III and Temozolomide Form VIII

Temozolomide Form III is prepared by contacting Temozolomide with a solvent including dimethylformamide (DMF), ethanol or a mixture of benzyl alcohol and isopropanol as a solvent component. In an embodiment, Temozolomide is dissolved in benzyl alcohol and subsequently crystallized by adding isopropanol, as a crystallization solvent. As noted above, Temozolomide Form III can also be formed by the heating of Temozolomide Form II to a temperature of about 120° C. The powder X-ray diffraction pattern of Temozolomide Form III crystals is substantially identical to the powder X-ray diffraction pattern of Temozolomide Form II crystals that have been heated to 120° C.

Temozolomide Form VIII is prepared by contacting Temozolomide with a solvent including acetone or methylene chloride as a solvent component. When the solvent component is acetone, the water content of the respective solvent is preferably less than 5% by weight water.

Figure 17:
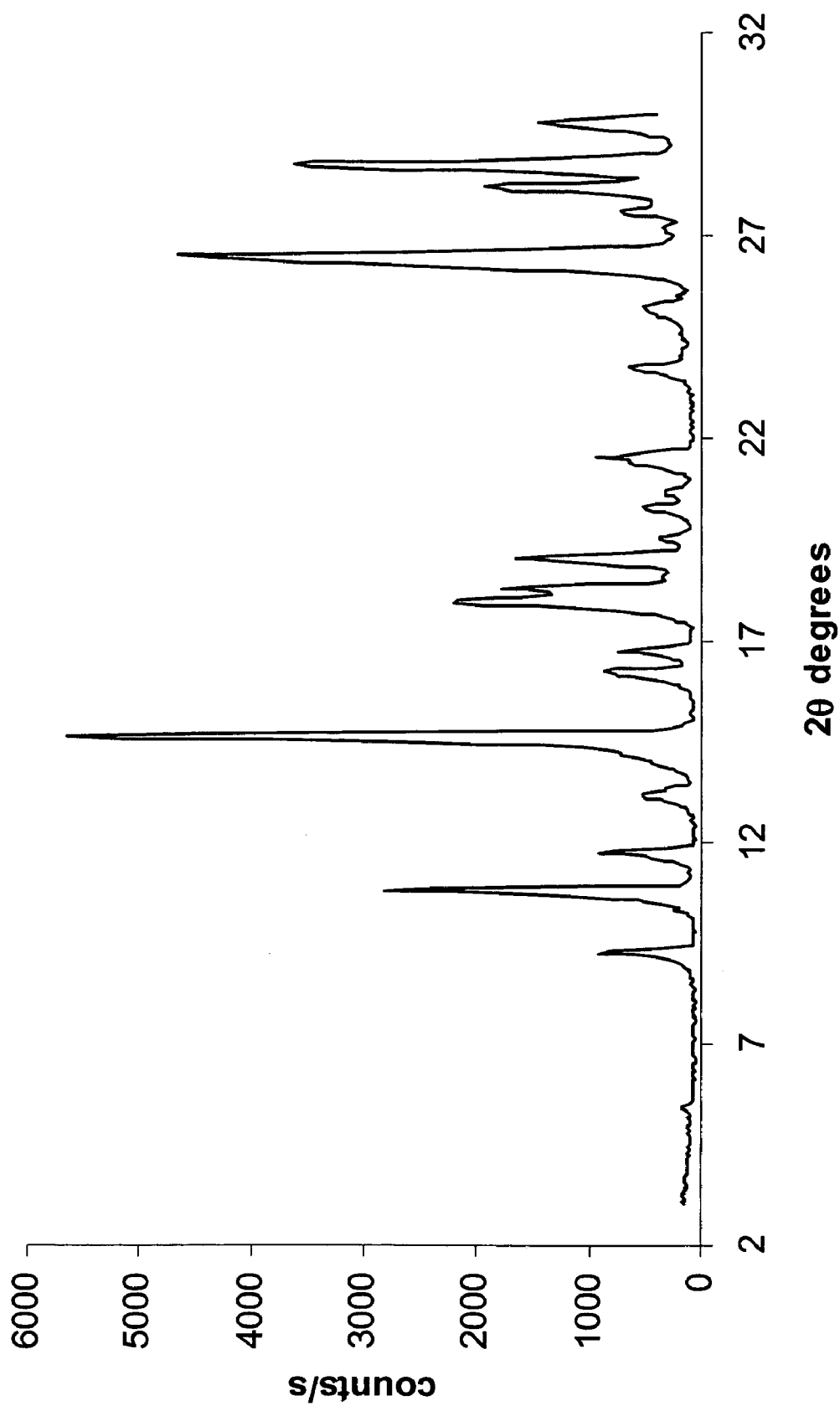
FIG. 17 presents an X-ray powder diffractogram of Temozolomide Form VIII.

The powder X-ray diffraction pattern of Temozolomide Form III (set forth in Table 3 below and further presented in FIG. 6) and of Temozolomide Form VIII (set forth in Table 4 below and further presented in FIG. 17) show a certain similarity with reflections characteristic for both Form III and Form VIII at about 10.8, 14.7 and 26.6±0.2°2θ and additional characteristic reflections at about 28.8 and 19.7±0.2°2θ. Temozolomide Form VIII shows unique reflections at about 9.3, 11.8 and 28.2±0.2°2θ.

Figure 7:
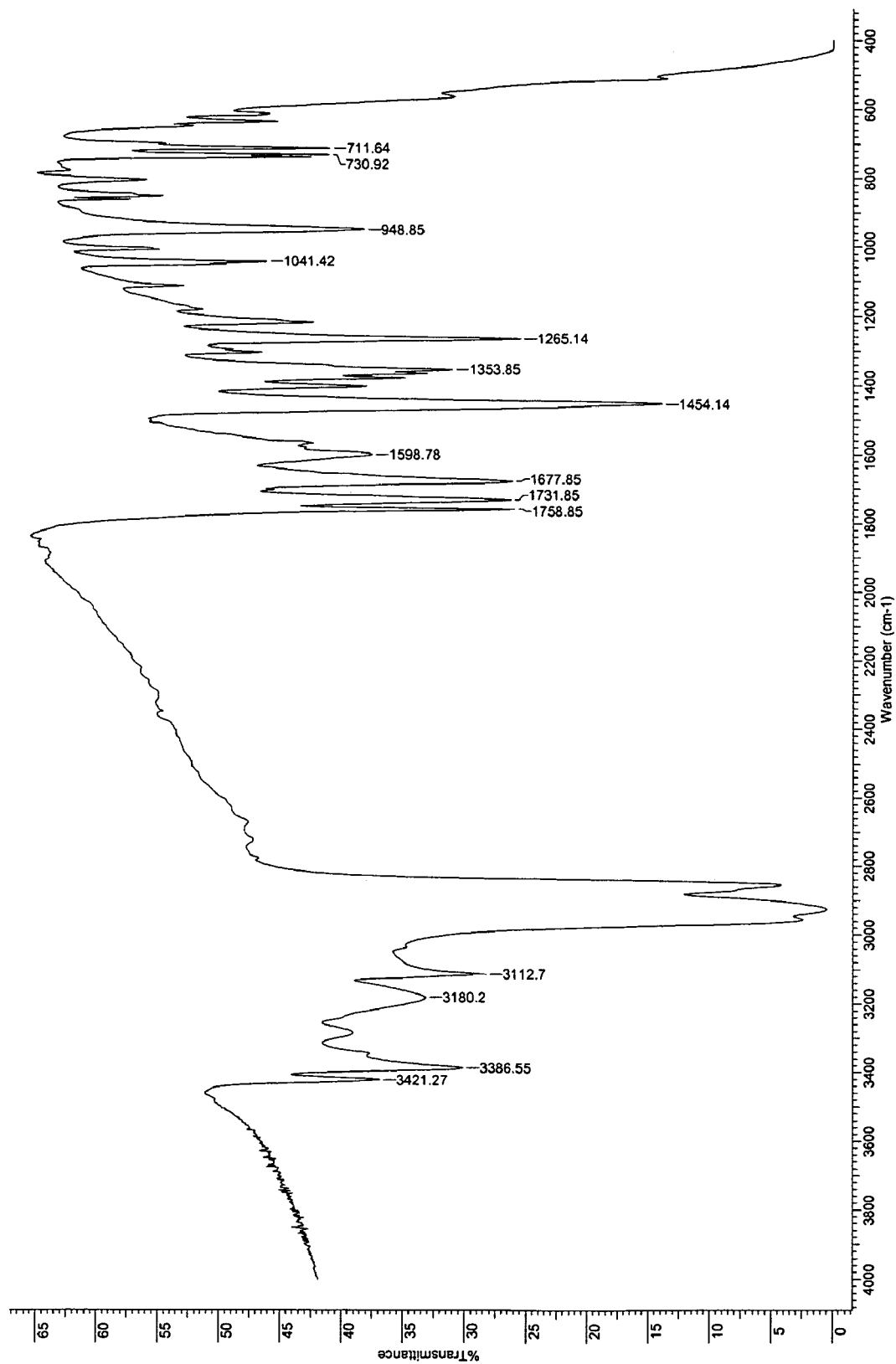
FIG. 7 presents an infrared spectrum of Temozolomide Form III.
Figure 18:
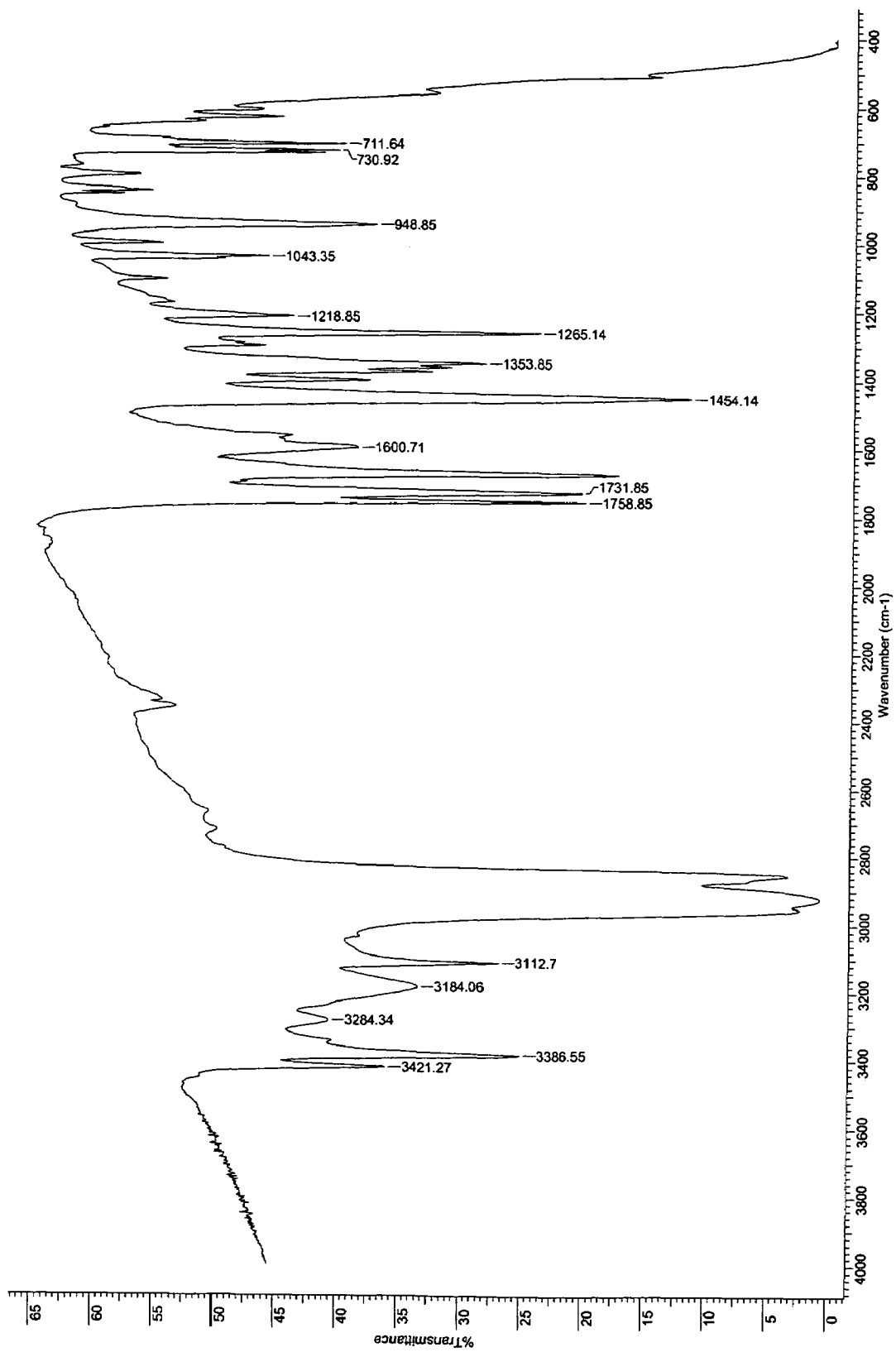
FIG. 18 presents an infrared spectrum of Temozolomide Form VIII.

The infrared absorption spectra of Temozolomide Form III and Form VIII are presented in FIG. 7 and FIG. 18, respectively. Characteristic absorption peaks are found at about 1678, 731 and 712±4 cm$^{-1}$ The DSC curve of Temozolomide Form III exhibits only one broad exothermic peak around 200° C. (data not shown), corresponding to decomposition.

The DSC curve of Temozolomide Form VIII exhibits only one exothermic peak that is completed by 200° C. (data not shown), corresponding to decomposition.

As is discussed above, the differences between Temozolomide Form III and Temozolomide Form VIII are clear. While Temozolomide Form III is prepared by contacting Temozolomide with a solvent including dimethylformamide (DMF), ethanol or a mixture of benzyl alcohol and isopropanol as a solvent component, Temozolomide Form VIII is prepared by crystallization of Temozolomide from a solvent including acetone or methylene chloride as a solvent component. Further, it is seen that the powder X-ray diffraction pattern of Temozolomide Form VIII shows reflections at about 9.3, 11.8 and 28.2±0.2°2θ which are not shown in the powder X-ray diffraction pattern of Temozolomide Form VIII.

TABLE 3

Form III - Powder X-ray diffraction reflection positions and intensities

| Rel. Intensity (%) | reflection (±0.2 °2θ) |
|---|---|
| 5 | 5.4 |
| 54 | 10.8 |
| 21 | 13.2 |
| 20 | 14.0 |
| 100 | 14.7 |
| 28 | 16.2 |
| 27 | 16.8 |
| 50 | 18.0 |
| 45 | 19.1 |
| 19 | 19.6 |
| 14 | 20.6 |
| 27 | 21.5 |
| 23 | 23.8 |
| 18 | 25.2 |
| 45 | 26.2 |
| 75 | 26.6 |
| 10 | 27.1 |
| 14 | 27.7 |
| 71 | 28.8 |
| 43 | 29.8 |
| 18 | 30.3 |

TABLE 4

Form VIII - Powder X-ray diffraction reflection positions and intensities

| reflection (±0.2 °2θ) | Rel. Intensity (%) |
|---|---|
| 5.3 | 4 |
| 9.3 | 16 |
| 10.8 | 50 |
| 11.8 | 16 |
| 13.2 | 9 |
| 14.6 | 100 |
| 16.2 | 15 |
| 16.8 | 13 |
| 18.0 | 39 |
| 19.0 | 30 |
| 19.5 | 7 |
| 20.3 | 9 |
| 20.6 | 6 |
| 21.5 | 17 |
| 23.7 | 12 |
| 25.2 | 9 |
| 26.5 | 82 |
| 27.1 | 6 |
| 27.6 | 13 |
| 28.2 | 34 |
| 28.7 | 64 |
| 29.8 | 26 |
| 30.3 | 9 |

Temozolomide Form IV

Temozolomide Form IV is prepared by contacting Temozolomide with a solvent including benzyl alcohol as a solvent component, the solvent being substantially devoid of isopropanol.

The powder X-ray diffraction pattern of Temozolomide Form IV (set forth in Table 5 below and further shown in FIG. 8) exhibits characteristic reflections at about 4.2 and 12.6±0.2°2θ and additional characteristic reflections at about 14.8 and 16.7±0.2°2θ.

Figure 9:
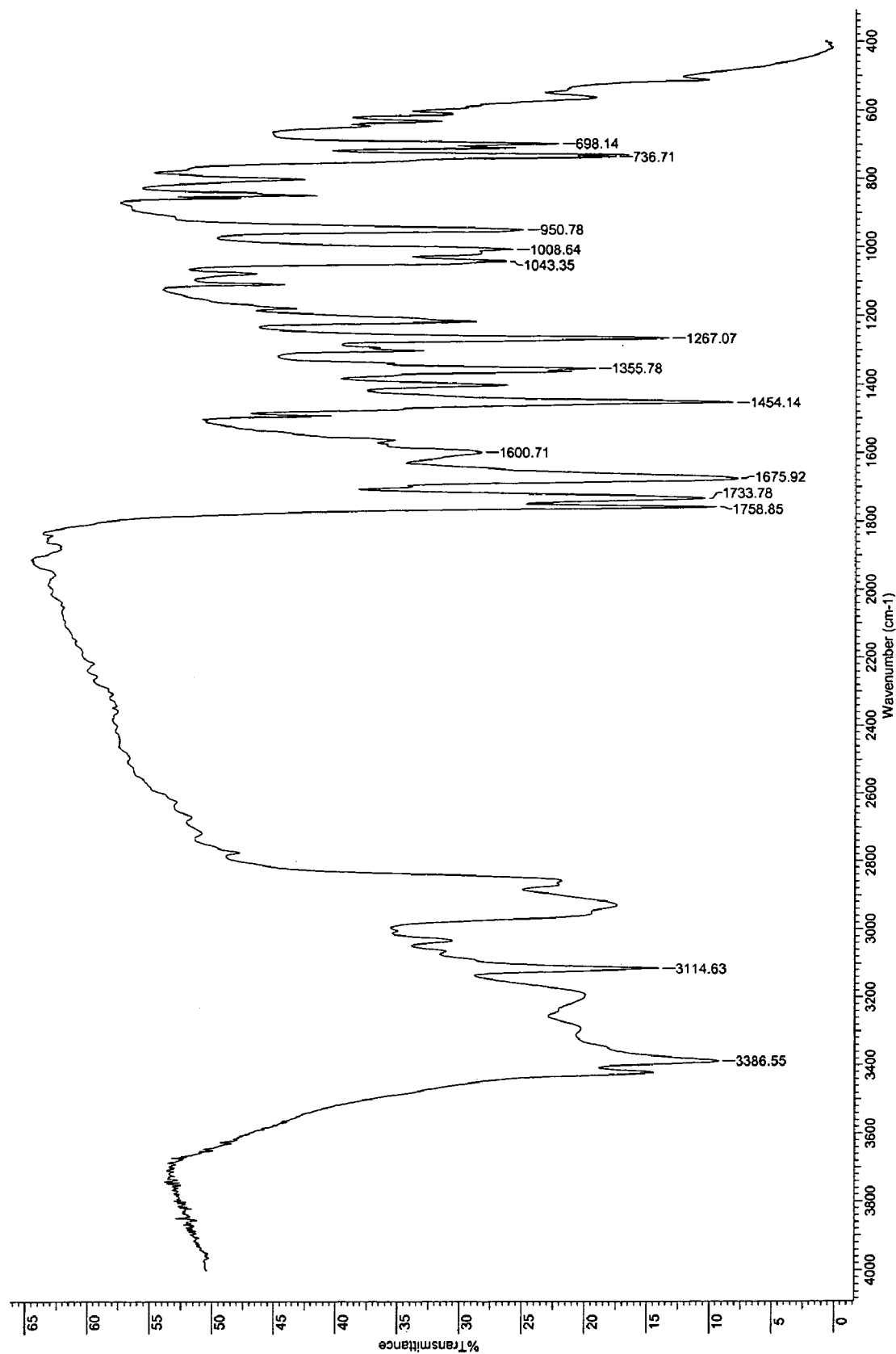
FIG. 9 presents an infrared spectrum of Temozolomide Form IV.

The infrared absorption spectrum of Temozolomide From IV is shown in FIG. 9. Characteristic absorption peaks are found at about 3387, 1759 and 1734±4 cm$^{-1}$ and additional characteristic absorption peaks are found at about 1009±4 cm$^{-1}$.

The DSC curve of Temozolomide Form IV exhibits only one exothermic peak that is completed by 200° C. (data not shown), corresponding to decomposition.

TABLE 5

Form IV - Powder X-ray diffraction reflection positions and intensities

| Rel. Intensity (%) | reflection (±0.2 °2θ) |
|---|---|
| 73 | 4.2 |
| 15 | 8.4 |
| 100 | 12.6 |
| 38 | 14.8 |
| 72 | 16.7 |
| 30 | 18.4 |
| 36 | 21.0 |
| 21 | 23.2 |
| 29 | 25.2 |
| 25 | 25.6 |
| 28 | 26.5 |
| 15 | 27.1 |
| 24 | 28.1 |
| 25 | 28.4 |
| 21 | 28.9 |
| 14 | 29.9 |
| 30 | 30.6 |

Temozolomide From V

Temozolomide Form V is prepared by contacting Temozolomide with a solvent including ethylene glycol as a solvent component.

Figure 10:
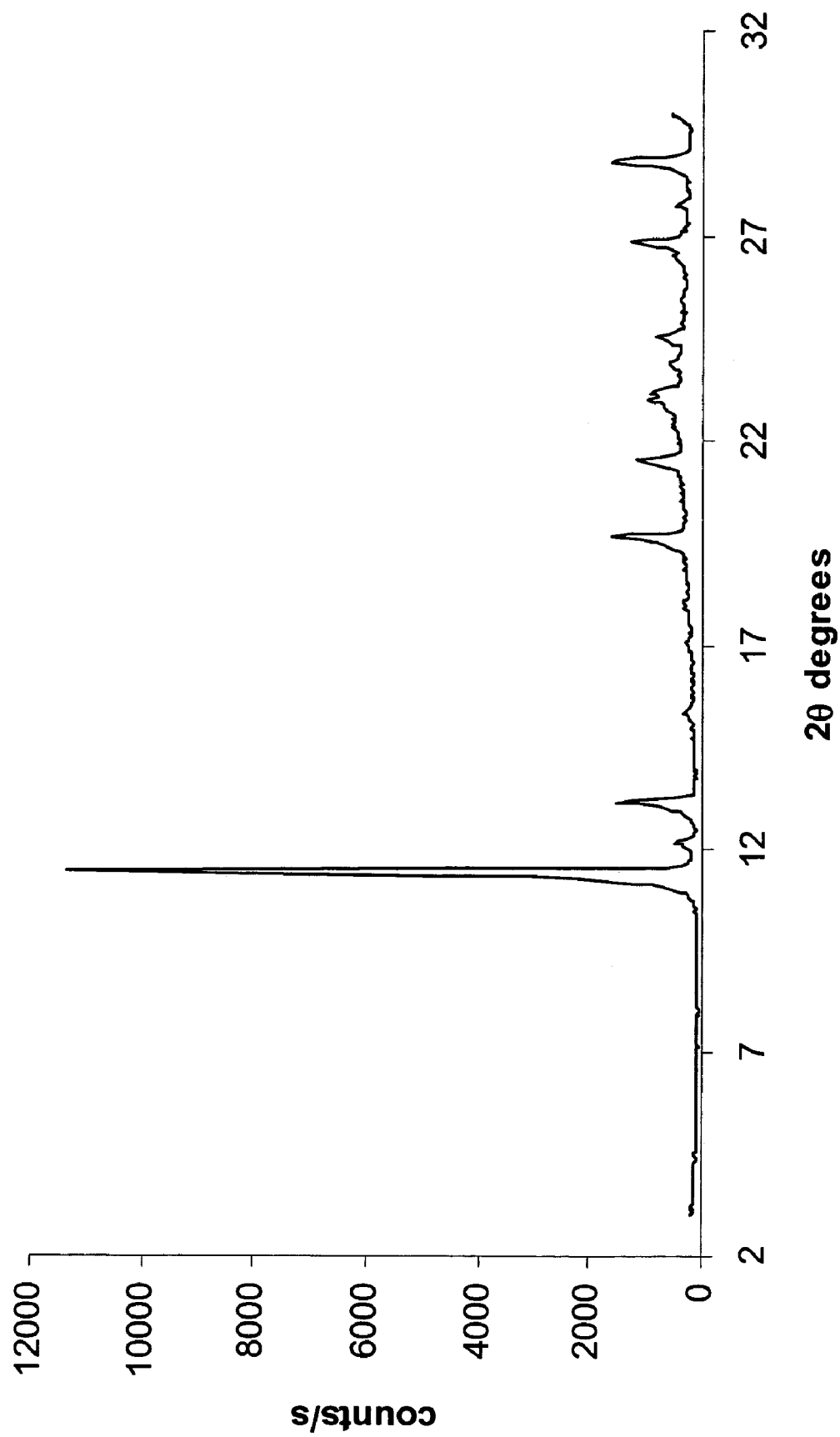
FIG. 10 presents an X-ray powder diffractogram of Temozolomide Form V.

The powder X-ray diffraction pattern of Temozolomide Form V (set forth in Table 6 below and further presented in FIG. 10) exhibits characteristic reflections at about 11.4, 13.2, 21.2, 26.5 and 26.8±0.2°2θ and an additional characteristic reflection at about 30.9±0.2°2θ.

Figure 11:
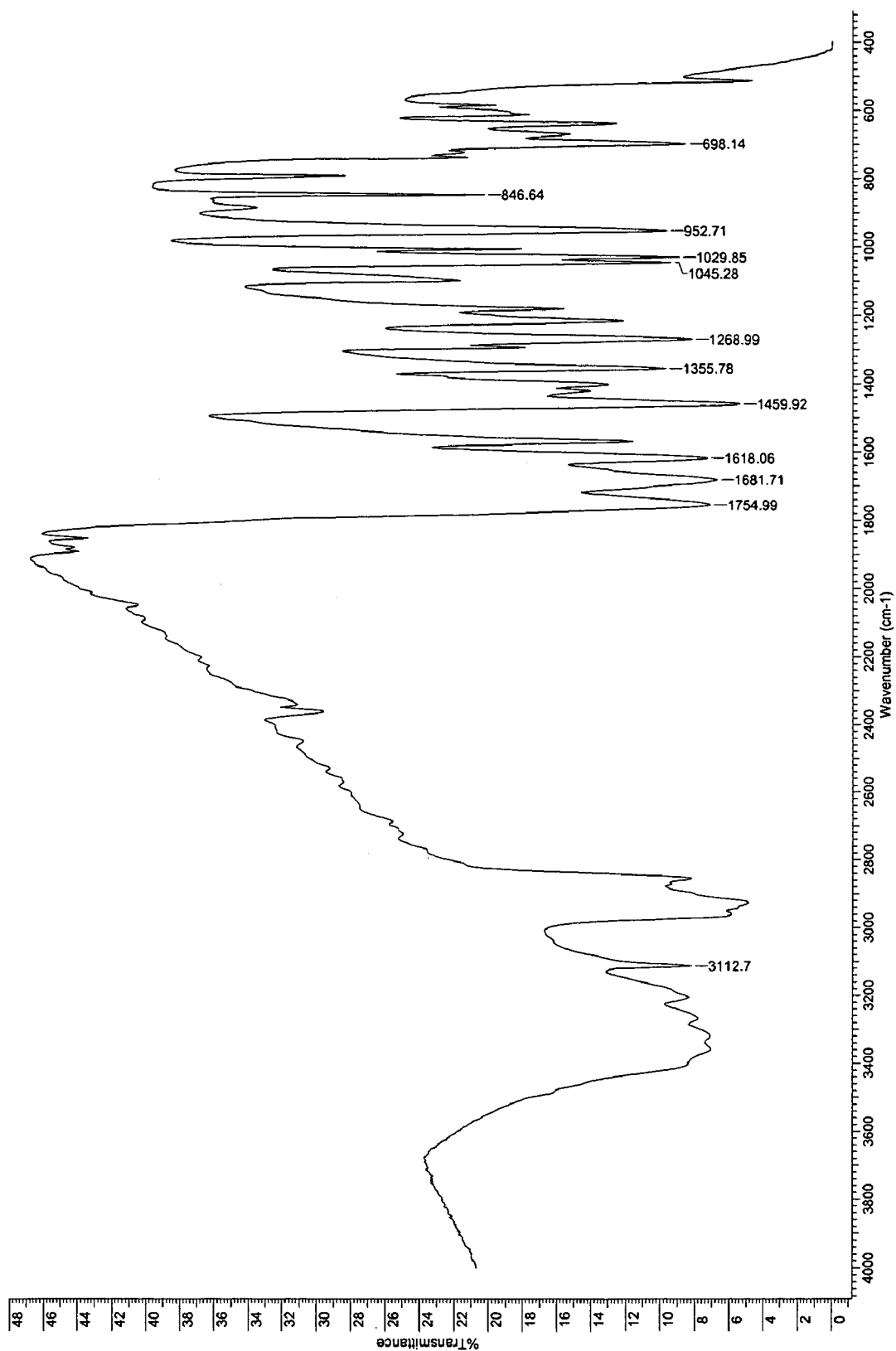
FIG. 11 presents an infrared spectrum of Temozolomide Form V.

The infrared absorption spectrum of Temozolomide From V is presented in FIG. 11. Characteristic peaks are found at about 3113, 1755 and 1619±4 cm$^{-1}$ and additional characteristic absorption peaks are found at about 1682 and 1356±4 cm$^{-1}$.

The DSC curve of Temozolomide Form V exhibits only one exothermic peak that is completed by 200° C. (data not shown), corresponding to decomposition.

TABLE 6

Form V - Powder X-ray diffraction reflection positions and intensities

| Rel. Intensity (%) | reflection (±0.2 °2θ) |
|---|---|
| 100 | 11.4 |
| 15 | 12.2 |
| 31 | 13.2 |

TABLE 6-continued

Form V - Powder X-ray diffraction reflection positions and intensities

| Rel. Intensity (%) | reflection (±0.2 °2θ) |
|---|---|
| 10 | 15.4 |
| 17 | 17.1 |
| 19 | 18.0 |
| 31 | 20.0 |
| 24 | 21.5 |
| 23 | 22.4 |
| 20 | 23.0 |
| 20 | 23.2 |
| 14 | 23.9 |
| 19 | 24.5 |
| 19 | 25.5 |
| 23 | 26.5 |
| 26 | 26.8 |
| 12 | 27.8 |
| 29 | 28.8 |
| 14 | 30.0 |
| 25 | 30.9 |

Temozolomide Form VI

Temozolomide From VI is prepared by contacting Temozolomide with a solvent including nitroethane as a solvent component.

Figure 12:
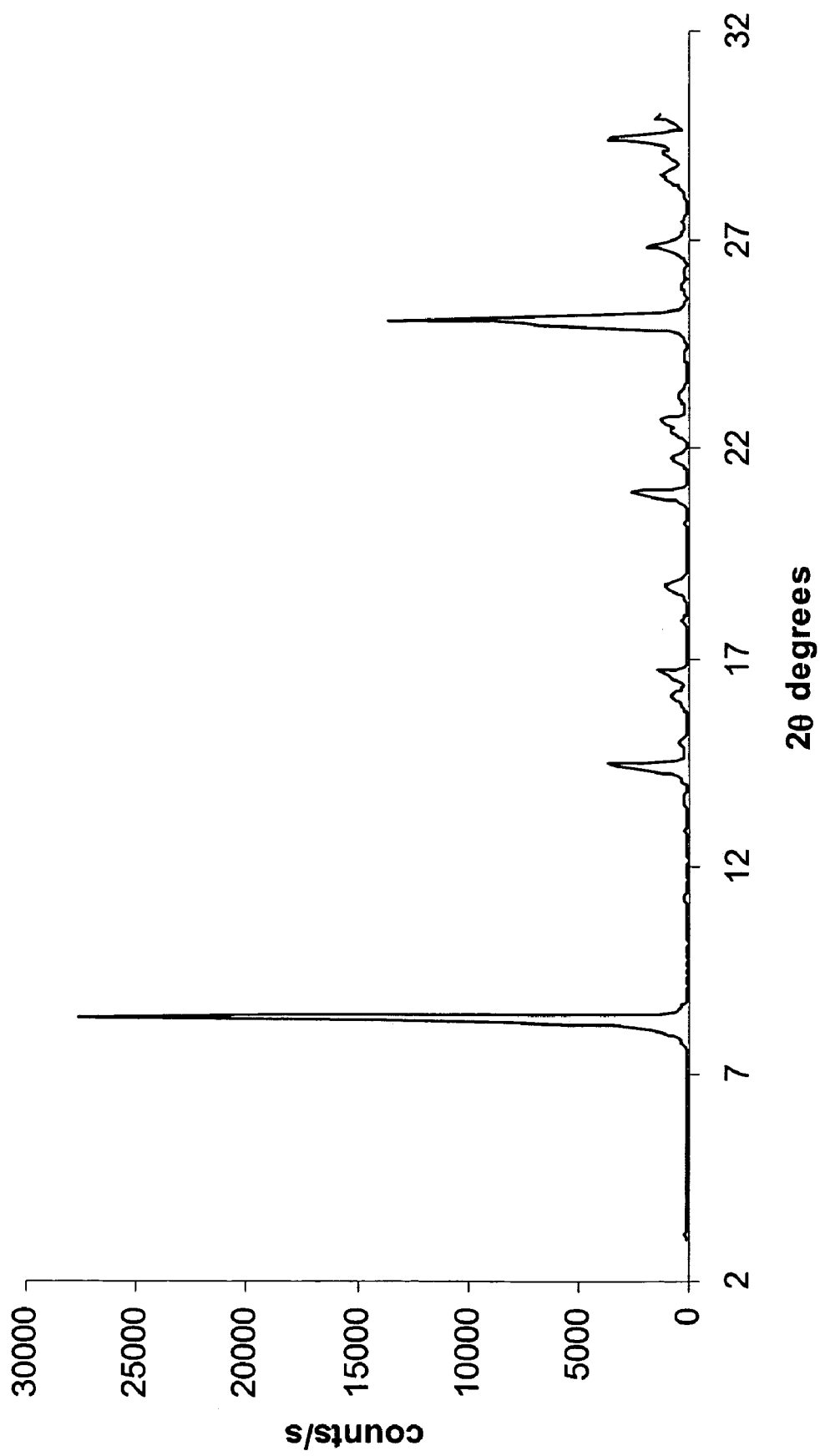
FIG. 12 presents an X-ray powder diffractogram of Temozolomide Form VI.

The powder X-ray diffraction pattern of Temozolomide Form VI (set forth in Table 7 below and further presented in FIG. 12) exhibits characteristics reflections at about 8.4, 14.4 and 25.1±0.2°2θ.

Figure 13:
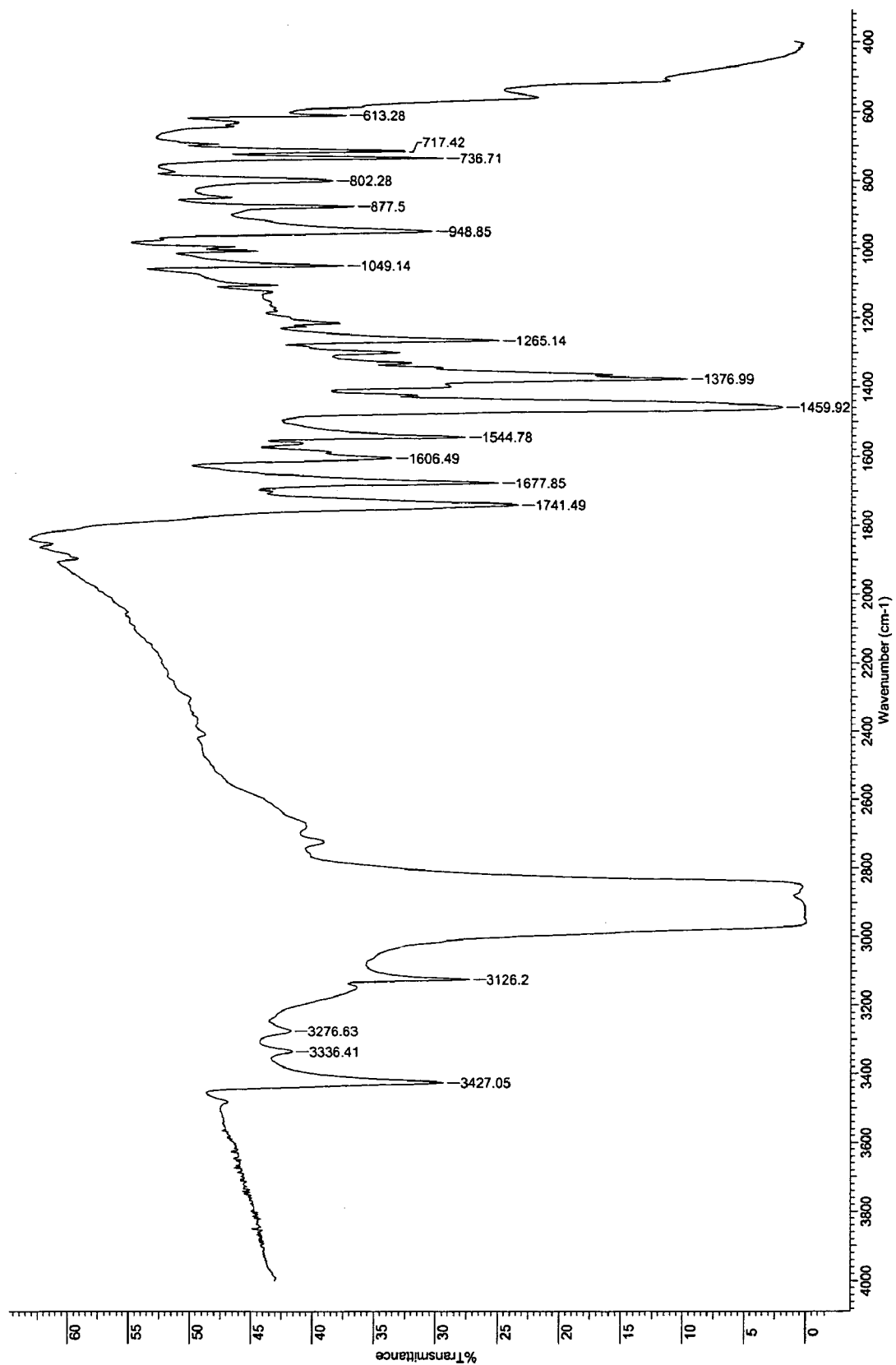
FIG. 13 presents an infrared spectrum of Temozolomide Form VI.

The infrared absorption spectrum of Temozolomide Form VI is presented in FIG. 13. Characteristic absorption peaks are found at about 3336, 3276, 1606 and 877±4 cm$^{-1}$ and additional characteristic absorption peaks are found at about 3126, 1741 and 802±4 cm$^{-1}$.

Figure 14:
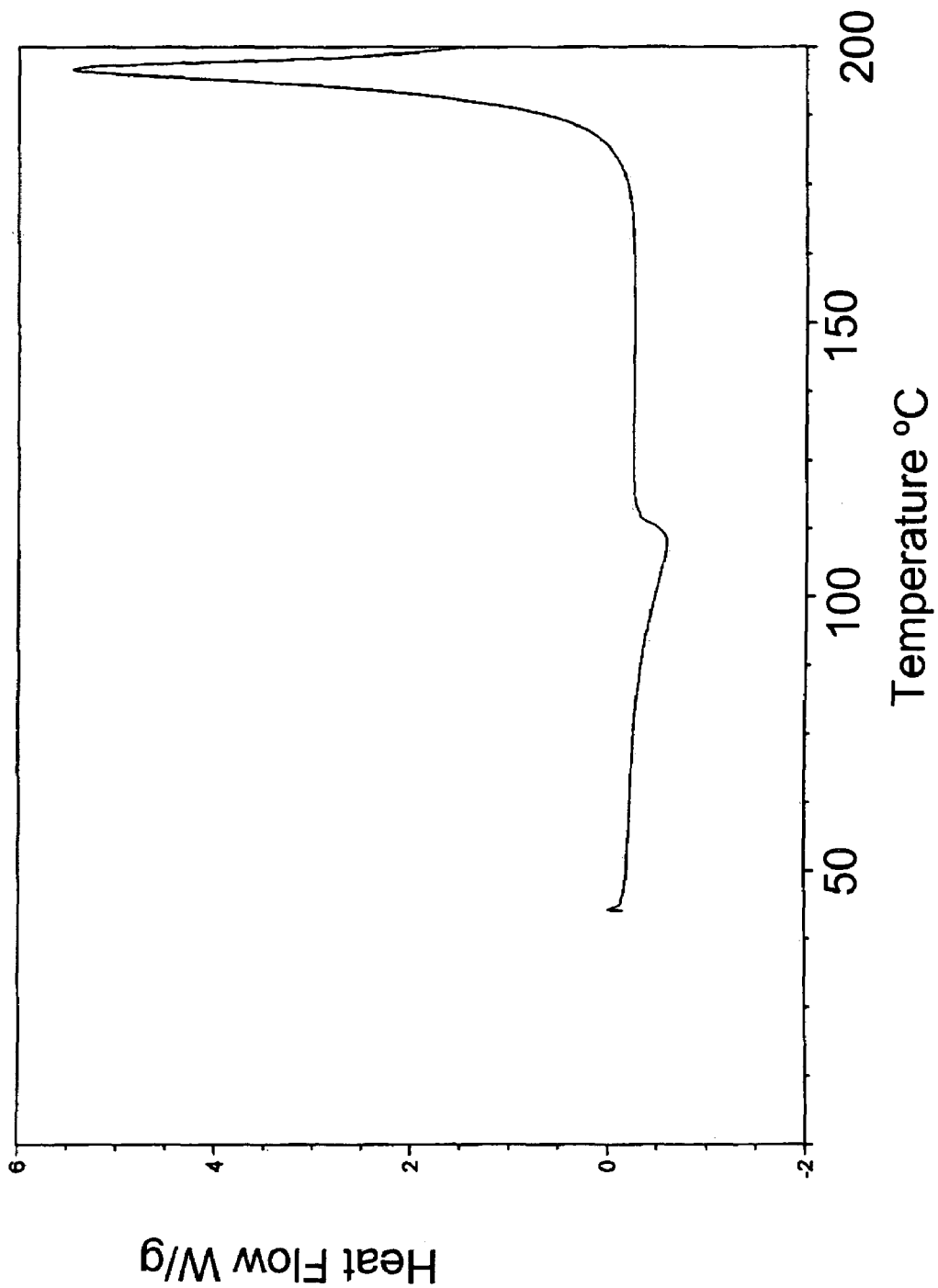
FIG. 14 presents a differential scanning calorimetry curve of Temozolomide Form VI.

Upon heating to 100-120° C., Temozolomide Form VI undergoes a non-reversible solid-solid transition to Temozolomide Form IX, vide infra. The transition of Temozolomide Form VI to Temozolomide Form IX is seen as an endothermic peak in the DSC curve of Temozolomide Form VI (FIG. 14).

TABLE 7

Form VI - Powder X-ray diffraction reflection positions and intensities

| Rel. Intensity (%) | reflection (±0.2 °2θ) |
|---|---|
| 100 | 8.4 |
| 8 | 10.8 |
| 4 | 11.3 |
| 6 | 12.0 |
| 8 | 12.9 |
| 9 | 13.5 |
| 9 | 13.8 |
| 33 | 14.4 |
| 8 | 15.0 |
| 12 | 16.1 |
| 12 | 16.5 |
| 18 | 16.7 |
| 7 | 17.5 |
| 5 | 17.9 |
| 15 | 18.8 |
| 2 | 20.2 |
| 26 | 21.0 |
| 11 | 21.8 |
| 12 | 22.4 |
| 16 | 22.7 |
| 7 | 23.3 |
| 8 | 23.8 |
| 4 | 24.2 |
| 60 | 25.1 |

TABLE 7-continued

| Form VI - Powder X-ray diffraction reflection positions and intensities | |
|---|---|
| Rel. Intensity (%) | reflection (±0.2 °2θ) |
| 5 | 25.9 |
| 10 | 26.3 |
| 21 | 26.9 |
| 5 | 27.5 |
| 15 | 28.6 |
| 15 | 29.0 |
| 32 | 29.4 |
| 17 | 29.9 |
| 8 | 30.9 |

Temozolomide From VII

Temozolomide Form VII is prepared by contacting Temozolomide with a solvent including dimethylsulfoxide (DMSO) as a solvent component.

Figure 15:
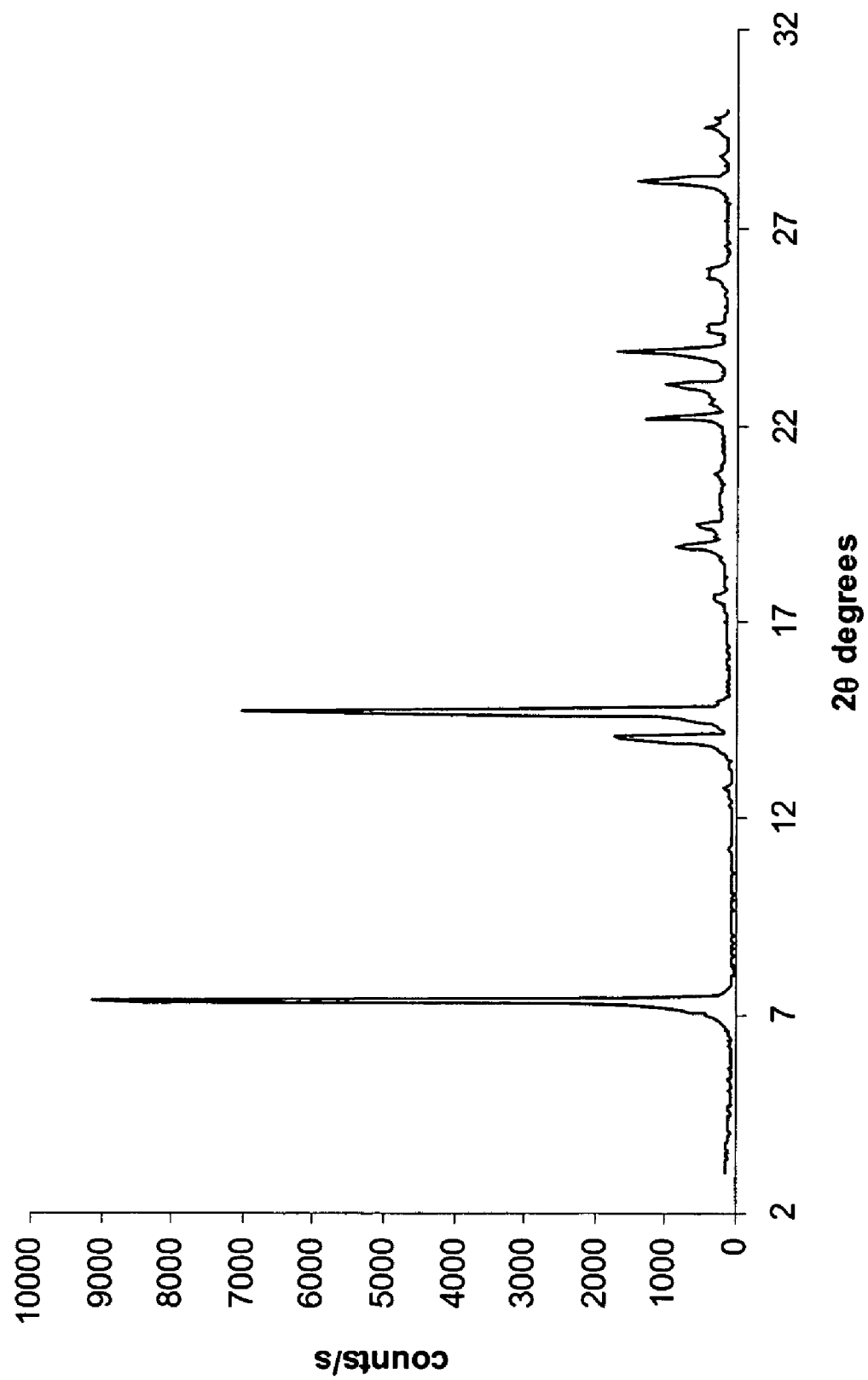
FIG. 15 presents an X-ray powder diffractogram of Temozolomide Form VII.

The powder X-ray diffraction pattern of Temozolomide Form VII (set forth in Table 8 below and further presented in FIG. 15) exhibits characteristics reflections at about 7.4 and 14.7±0.2°2θ, an additional characteristic reflection at about 14.1 and 28.2±0.2°2θ and a further additional characteristic reflections at about 22.2, 23.0 and 23.9±0.2°2θ.

Figure 16:
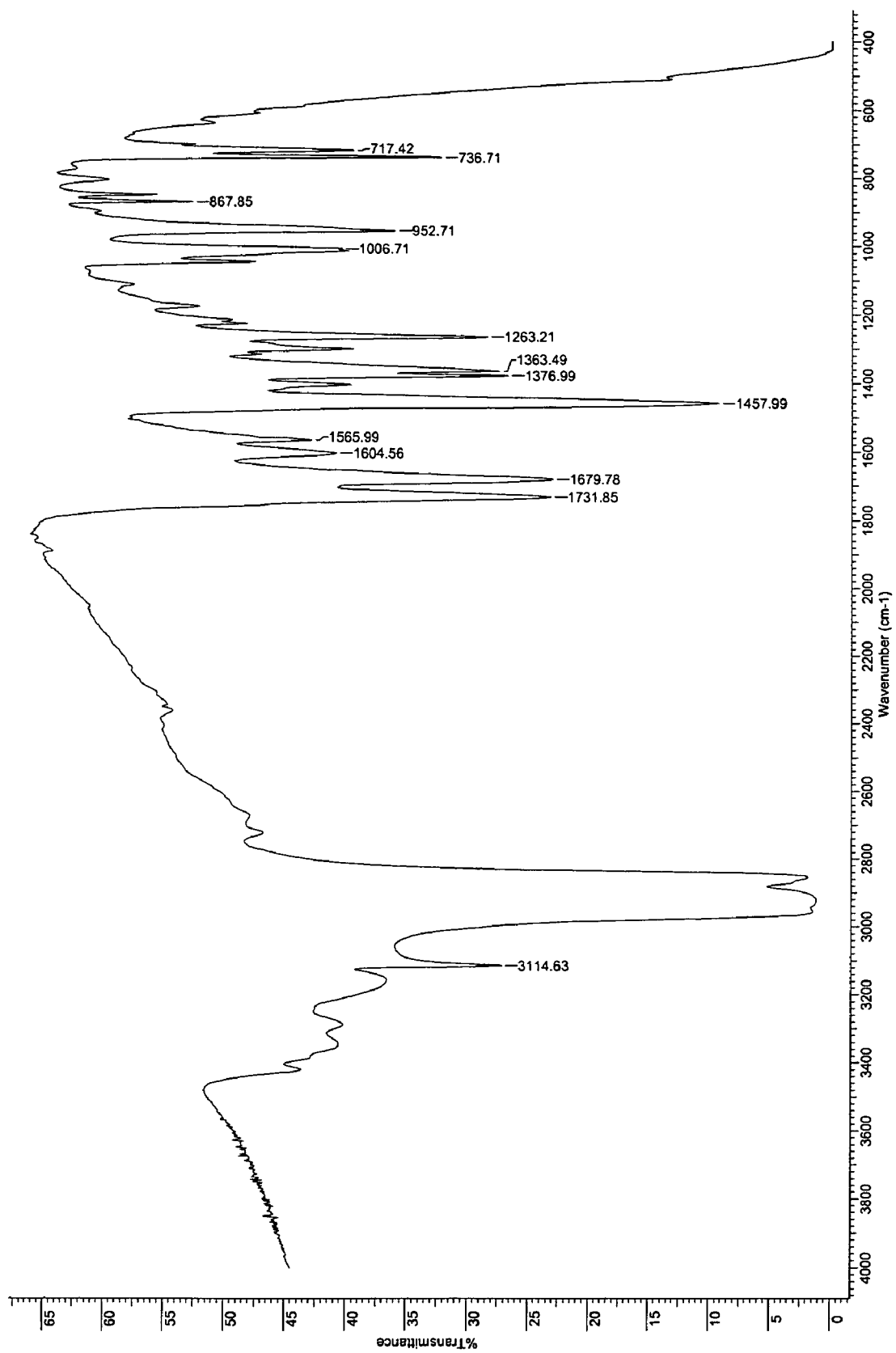
FIG. 16 presents an infrared spectrum of Temozolomide Form VII.

The infrared absorption spectrum of Temozolomide Form VII is presented in FIG. 16. Characteristic absorption peaks are found at about 3115, 1732, 1605 and 1566±4 cm$^{-1}$ and additional characteristic absorption peaks are found at about 1263±4 cm$^{-1}$.

TABLE 8

| Form VII - Powder X-ray diffraction reflection positions and intensities | |
|---|---|
| Rel. Intensity (%) | reflection (±0.2 °2θ) |
| 100 | 7.4 |
| 12 | 11.2 |
| 6 | 12.8 |
| 38 | 14.1 |
| 89 | 14.7 |
| 10 | 17.6 |
| 23 | 19.0 |
| 17 | 19.5 |
| 19 | 20.1 |
| 21 | 20.8 |
| 30 | 22.2 |
| 23 | 22.5 |
| 25 | 23.0 |
| 37 | 23.9 |
| 12 | 24.5 |
| 12 | 25.8 |
| 12 | 26.0 |
| 32 | 28.2 |
| 18 | 28.8 |
| 21 | 29.6 |
| 20 | 31.1 |

Temozolomide Form IX

Temozolomide Form IX is prepared by heating Temozolomide Form VI to a temperature at least about 110° C., preferably about 120° C.

Figure 19:
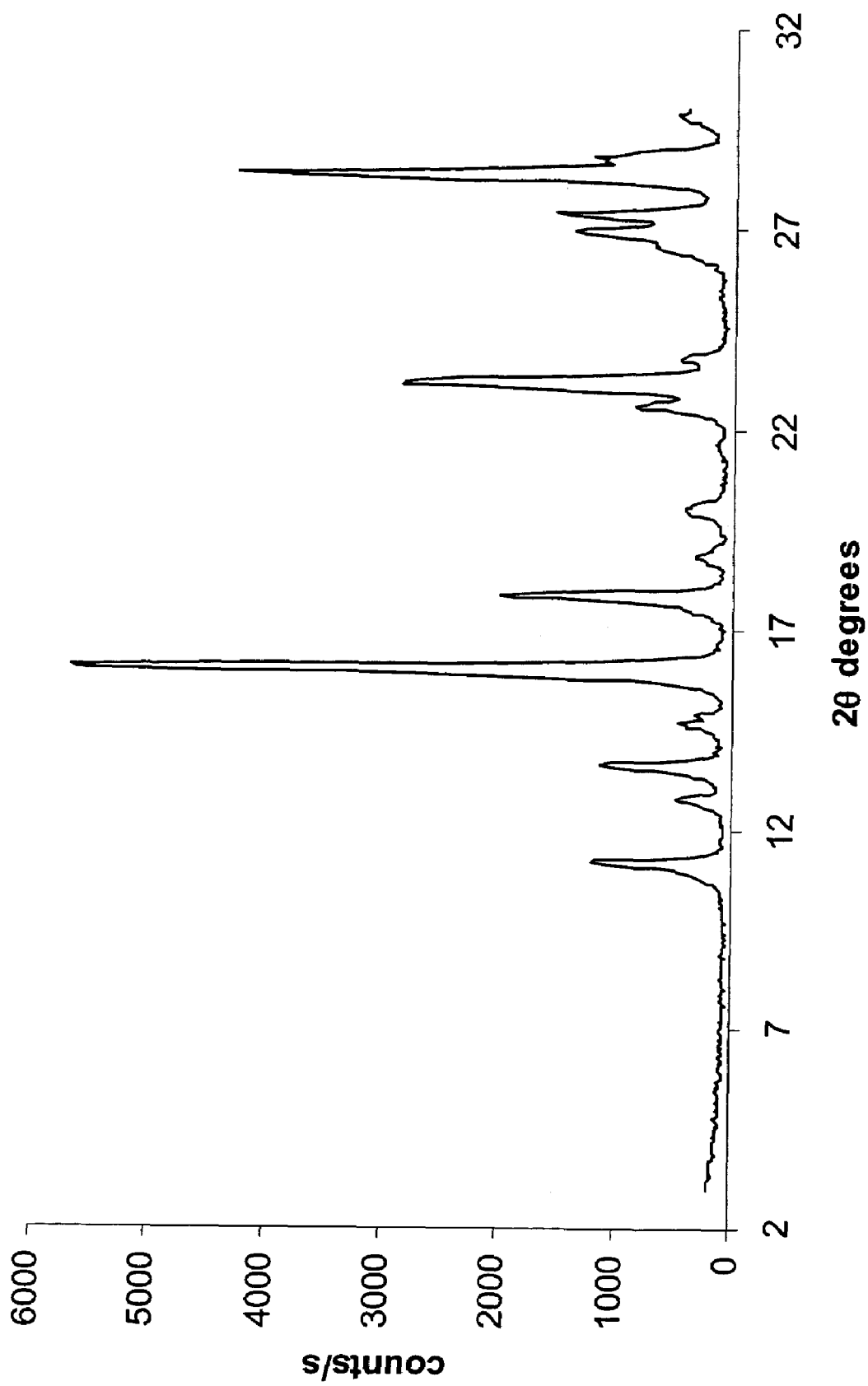
FIG. 19 presents an X-ray powder diffractogram of Temozolomide Form IX.

The powder X-ray diffraction pattern of Temozolomide Form IX (set forth in Table 9 below and further presented in FIG. 19) exhibits characteristic reflections at about 13.7, 16.1, 23.2 and 30.1±0.2°2θ, an additional characteristic reflection at about 26.4±0.2°2θ and a further additional characteristic reflections at about 17.5 and 19.9±0.2°2θ.

Figure 20:
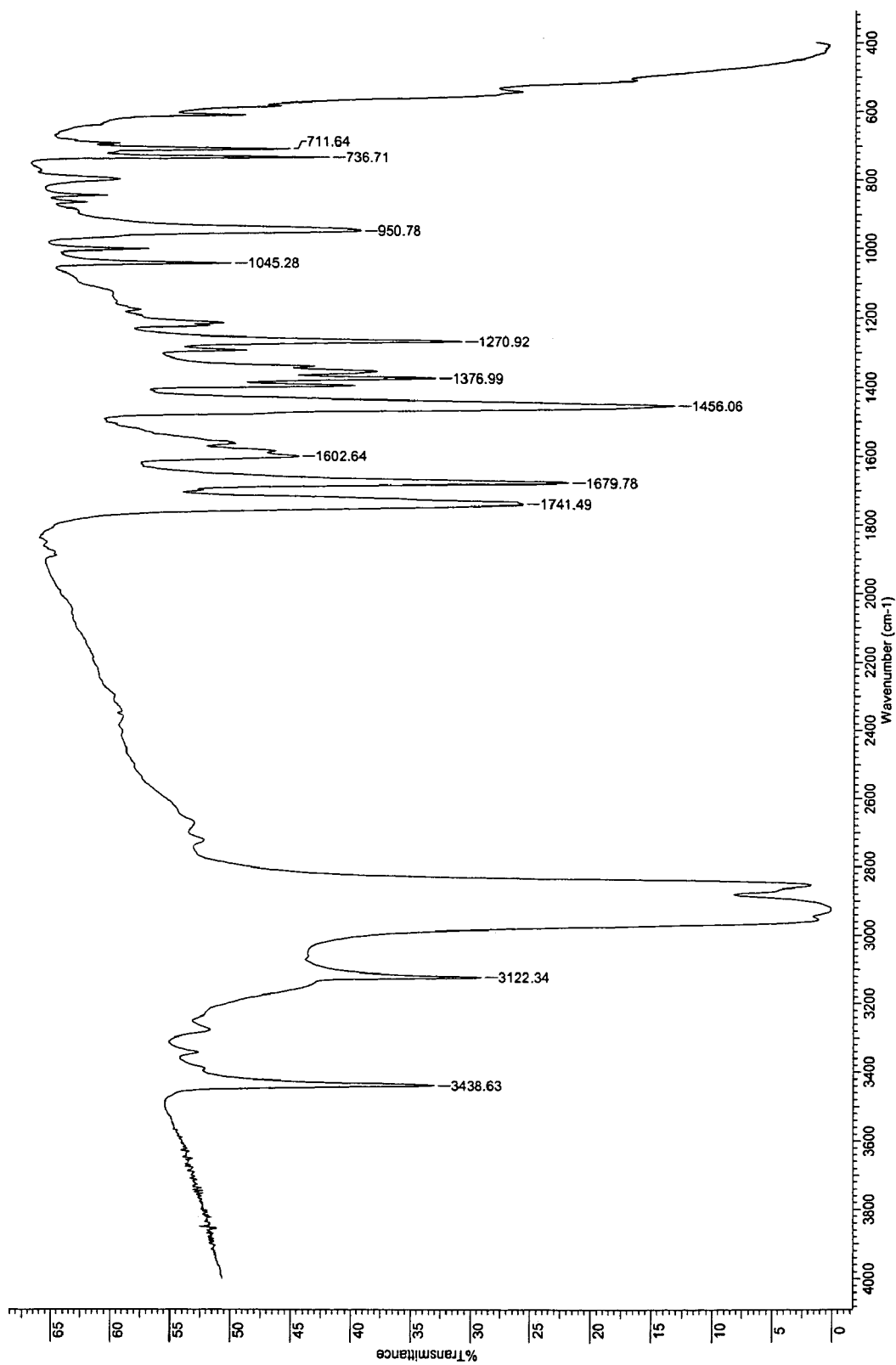
FIG. 20 presents an infrared spectrum of Temozolomide Form IX.

The infrared absorption spectrum of Temozolomide Form IX is shown in FIG. 20. Characteristic absorption peaks are found at about 3439, 3122, 1741 and 1271±4 cm$^{-1}$.

TABLE 9

| Form IX - Powder X-ray diffraction reflection positions and intensities | |
|---|---|
| reflection (±0.2 °2θ) | Rel. Intensity (%) |
| 11.2 | 38 |
| 12.8 | 23 |
| 13.7 | 41 |
| 14.6 | 38 |
| 15.0 | 25 |
| 16.1 | 100 |
| 17.5 | 35 |
| 17.9 | 49 |
| 18.9 | 35 |
| 19.9 | 10 |
| 20.2 | 7 |
| 21.7 | 23 |
| 22.6 | 31 |
| 23.2 | 73 |
| 23.8 | 9 |
| 26.4 | 41 |
| 27.0 | 37 |
| 27.4 | 43 |
| 28.4 | 89 |
| 28.8 | 13 |
| 29.8 | 39 |
| 30.1 | 41 |

Pharmaceutical Compositions Including Temozolomide Forms I-IX

Similar to prior art Temozolomide crystalline forms, Temozolomide forms I-IX are also generally useful for the preparation of pharmaceutical compositions where Temozolomide is an active ingredient. The purpose of a pharmaceutical composition is to facilitate administration of a compound to a subject. The term "active ingredient" refers to a compound which is accountable for a biological effect of a pharmaceutical composition.

Generally a pharmaceutical composition of the present invention includes at least one of forms I-IX of Temozolomide (as a sole active ingredient or together with other active ingredients) together with a pharmaceutically acceptable carrier. A pharmaceutically acceptable carrier generally includes such components as antibacterial agents, antioxidant agents, binding agents, buffering agents, bulking agents coloring agents, diluents, disintegrants, emulsifying agents, excipients, flavoring agents, glidants, lubricants, skin penetration enhancers, sweetening agents, viscosity modifying agents and combinations thereof.

A pharmaceutical composition of the present invention can include, in addition to one or more of Temozolomide Forms I-IX, Temozolomide that is not of Forms I-IX, or an additional non-Temozolomide active ingredient.

A pharmaceutical composition of the present invention is provided in any delivery form appropriate for delivery of Temozolomide, and is preferably provided as capsules.

The terms "physiologically acceptable carrier" and "pharmaceutically acceptable carrier" which may be used interchangeably to refer to a carrier or a diluent that does not cause significant irritation to an organism and does not abrogate the biological activity and properties of the administered compound.

Herein the term "excipient" refers to an inert substance added to a pharmaceutical composition to facilitate administration of a compound. Suitable excipients include, but are not limited to, calcium carbonate, calcium phosphate, various sugars and types of starch, cellulose derivatives, gelatin, vegetable oils and polyethylene glycols.

Techniques for formulation and administration of compounds as medicaments may be found in "Remington's Pharmaceutical Sciences," Mack Publishing Co., Easton, Pa., latest edition, which is incorporated herein by reference.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions of the present invention may be formulated in conventional manner using one or more physiologically acceptable carriers comprising excipients and auxiliaries, which facilitate processing of the active compounds into preparations which, can be used pharmaceutically. Proper formulation is dependent upon the route of administration chosen.

Pharmaceutical compositions suitable for use in context of the present invention include compositions where the active ingredients are contained in an amount effective to achieve the intended purpose. More specifically, a therapeutically effective amount means an amount of active ingredient effective to cure a condition, treat a condition, prevent a condition, treat symptoms of a condition, cure symptoms of a condition, ameliorate symptoms of a condition, treat effects of a condition, ameliorate effects of a condition, and prevent results of a condition in which treatment by Temozolomide is beneficial.

A pharmaceutical composition of the present invention is preferably fashioned as a hard capsule containing between about 1 mg and about 250 mg Temozolomide more preferably 5 mg, 20 mg, 100 mg or 250 mg of the desired Temozolomide crystalline form or combination of Temozolomide crystalline forms.

Preferably, a pharmaceutical composition of the present invention is packaged in a packaging material and identified in or on the packaging material, for use for a need selected from the group consisting of curing a condition, treating a condition, preventing a condition, treating symptoms of a condition, curing symptoms of a condition, ameliorating symptoms of a condition, treating effects of a condition, ameliorating effects of a condition, and preventing results of a condition in which treatment by Temozolomide is beneficial.

Exemplary conditions for which the composition is beneficial include cancer, brain cancer, breast cancer, refractory anaplastic astrocytoma, malignant glioma, glioblastoma multiforme and anaplastic astrocytoma.

Preparation of Pharmaceutical Composition Including Temozolomide Forms I-IX:

A pharmaceutical composition of the present invention is preferably prepared by combining one or more of Temozolomide Form I-IX with a pharmaceutically acceptable carrier and when applicable, further active ingredients, as described hereinabove.

Methods of Treatment Using Temozolomide Forms I-IX:

The method of treatment of the present invention includes the administration of a pharmaceutically effective amount of one or more of Temozolomide Forms I-IX to a mammal (preferably a human) in need thereof. Most preferred is that the Temozolomide is administered as a pharmaceutical composition of the present invention as described above.

A need for administration arises, for example, when the mammal has a medical condition such as cancer, brain cancer, breast cancer, refractory anaplastic astrocytoma, malignant glioma, glioblastoma multiforme and anaplastic astrocytoma. Such a need includes curing the condition, treating the condition, preventing the condition, treating symptoms of the condition, curing symptoms of the condition, ameliorating symptoms of the condition, treating effects of the condition, ameliorating effects of the condition, and preventing results of the condition. By treating or preventing is meant that an administered Temozolomide is used as a therapeutic, prophylactic or ameliorative agent, whether with respect to a pathology, condition or disorder, a symptom thereof or an effect thereof.

Administration of the Temozolomide crystalline forms of the present invention is preferably effected orally.

A therapeutically (or pharmaceutically) effective amount means an amount of active ingredient needed to achieve the desired outcome, which is generally to prevent, alleviate or ameliorate a condition or symptoms of the condition.

Depending on the severity and responsiveness of the condition to be treated, dosing can also be a single administration of a slow release composition, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

That said, in the art an acceptable pharmaceutically effective amount of Temozolomide for treatment of a human generally between about 1 mg and about 250 mg Temozolomide and specifically is about 5 mg, about 20 mg, about 100 mg or about 250 mg per dose.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples that, together with the above descriptions, illustrate the invention in a non-limiting fashion.

Generally, the nomenclature used herein and the laboratory procedures utilized in the present invention include chemical and analytical techniques with which on skilled in the art is familiar. Unless otherwise defined, technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Experimental Methods

Powder X-ray diffraction patterns were acquired using a Philips PW 1050-70 X-ray Diffractometer. System description: $K_\alpha 1 = 1.54178$ Å, voltage 40 kV, current 28 mA, diversion slit=1°, receiving slit=0.2 mm, scattering slit-1° with a Graphite monochromator. Experiment parameters: pattern measured between $2\theta=4°$ and $2\theta=30°$ with 0.05° increments; count time 0.5 second per increment. The accuracy of the diffraction angles determined is approximately ±0.2°2θ.

Infrared (IR) spectra were acquired using a Nicolet™ Avatar™ 360 Fourier-transform Infra-Red Spectrometer with Omnic software version 5.2. All samples were run as Nujol® mulls held between NaCl plates. The accuracy of the wave numbers $v_{max}$ determined is approximately ±4 cm$^{-1}$.

Differential scanning calorimetry (DSC) graphs were recorded using a TA Instruments Q1000 Thermal Analyzer with Universal software (version 3.88). Samples were analyzed inside crimped 40 µl Aluminum pans at a heating rate of 5° C./min.

Thermogravimetric analysis (TGA) was performed using a TA Instruments Q500 Thermal Analyzer with Universal Software (version 3.88). Samples were analyzed inside platinum baskets at heating rate of 5° C./min.

Experimental Results

Example 1

Preparation of Temozolomide Form I

In a 100 ml three necked round bottom flask equipped with a reflux condenser, a thermometer and a magnetic stirrer, Temozolomide (1 gram, obtained from a commercial source) was dissolved in 30 ml of pyridine. The solution was heated, using an oil bath, to 90° C., and left inside the hot oil to cool down to 25° C. The resulting crystals (0.8 gram) were filtered and left to dry inside a hood. The X-ray powder diffractogram of the product is presented in FIG. 1 and reflections thereof listed in Table 1 above. The IR spectrum of the product is presented in FIG. 2.

Example 2

Preparation of Temozolomide Form I

In a 500 ml three necked round bottom flask equipped with a reflux condenser, a thermometer and a magnetic stirrer, Temozolomide (1 gram) was dissolved in 115 ml of 8:15 isopropanol:pyridine mixture. The solution was heated using an oil bath to 90° C., and then cooled in ice. The resulting crystals (0.6 gram) were filtered and left to dry inside a hood.

Example 3

Preparation of Temozolomide Form I

In a 100 ml three necked round bottom flask equipped with a reflux condenser, a thermometer and a magnetic stirrer, Temozolomide (1 gram) was dissolved in 30 ml of pyridine. The solution was heated using an oil bath to 90° C., and then cooled in ice. The resulting crystals (0.6 gram) were filtered and left to dry inside a hood.

Example 4

Preparation of Temozolomide Form II

In a 100 ml three necked round bottom flask equipped with a reflux condenser, a thermometer and a magnetic stirrer, Temozolomide (1 gram) was dissolved in 30 ml of pyridine. The solution was heated using an oil bath to 90° C., and left inside the hot oil to cool down to 25° C. The resulting crystals (0.8 gram) were filtered and dried in vacuum at 30° C. in vacuum. The X-ray powder diffractogram of the product is presented in FIG. 2 and reflections thereof listed in Table 2 above. The IR spectrum of the product is presented in FIG. 3. The differential scanning calorimetry curve of the product is presented in FIG. 5.

Example 5

Preparation of Temozolomide Form II

Temozolomide Form I (1 gram) prepared according to Example 1 was heated at 30° C. for 8 hours. The X-ray powder diffractogram of the product was substantially identical to that of Temozolomide Form II of Example 4.

Example 6

Preparation of Temozolomide Form III

In a 100 ml three necked round bottom flask equipped with a reflux condenser, a thermometer and a magnetic stirrer, Temozolomide (1 gram) was dissolved in 270 ml of ethanol. The solution was heated using an oil bath to reflux, and then cooled in ice. The resulting crystals (0.5 gram) were filtered and left to dry inside a hood. The X-ray powder diffractogram of the product is presented in FIG. 6 and reflections thereof listed in Table 3 above. The IR spectrum of the product is presented in FIG. 7.

Example 7

Preparation of Temozolomide Form III

In a 100 ml three-necked round bottom flask equipped with a reflux condenser, a thermometer and a magnetic stirrer, Temozolomide (1 gram) was dissolved in 20 ml of dimethylformamide (DMF). The solution was heated using an oil bath to 90° C., and then left to cool to room temperature. The resulting crystals (0.6 gram) were filtered and dried in vacuum at 30° C.

Example 8

Preparation of Temozolomide Form III

In a 100 ml three necked round bottom flask equipped with a reflux condenser, a thermometer and a magnetic stirrer, Temozolomide (1 gram) was dissolved in 20 ml of benzyl alcohol. The solution was heated using an oil bath to 90° C. Isopropanol (20 ml) was added dropwise until the beginning of crystallization. The crystals were left inside the solution to cool to room temperature. The resulting crystals (0.6 gram) were filtered and dried in vacuum at 30° C.

Example 9

Preparation of Temozolomide Form III

Temozolomide Form II (1 gram) prepared according to Example 4 was heated at 120° C. for 15 minutes. The X-ray powder diffractogram of the product was substantially identical to that of Temozolomide Form III of Example 8.

Example 10

Preparation of Temozolomide Form IV

In a 100 ml three necked round bottom flask equipped with a reflux condenser, a thermometer and a magnetic stirrer, Temozolomide (1 gram) was dissolved in 36 ml of benzyl alcohol. The solution was heated using an oil bath to 100° C., and then left to cool to room temperature. The resulting crystals (0.75 gram) were filtered and dried in vacuum at 30° C.

Figure 8:
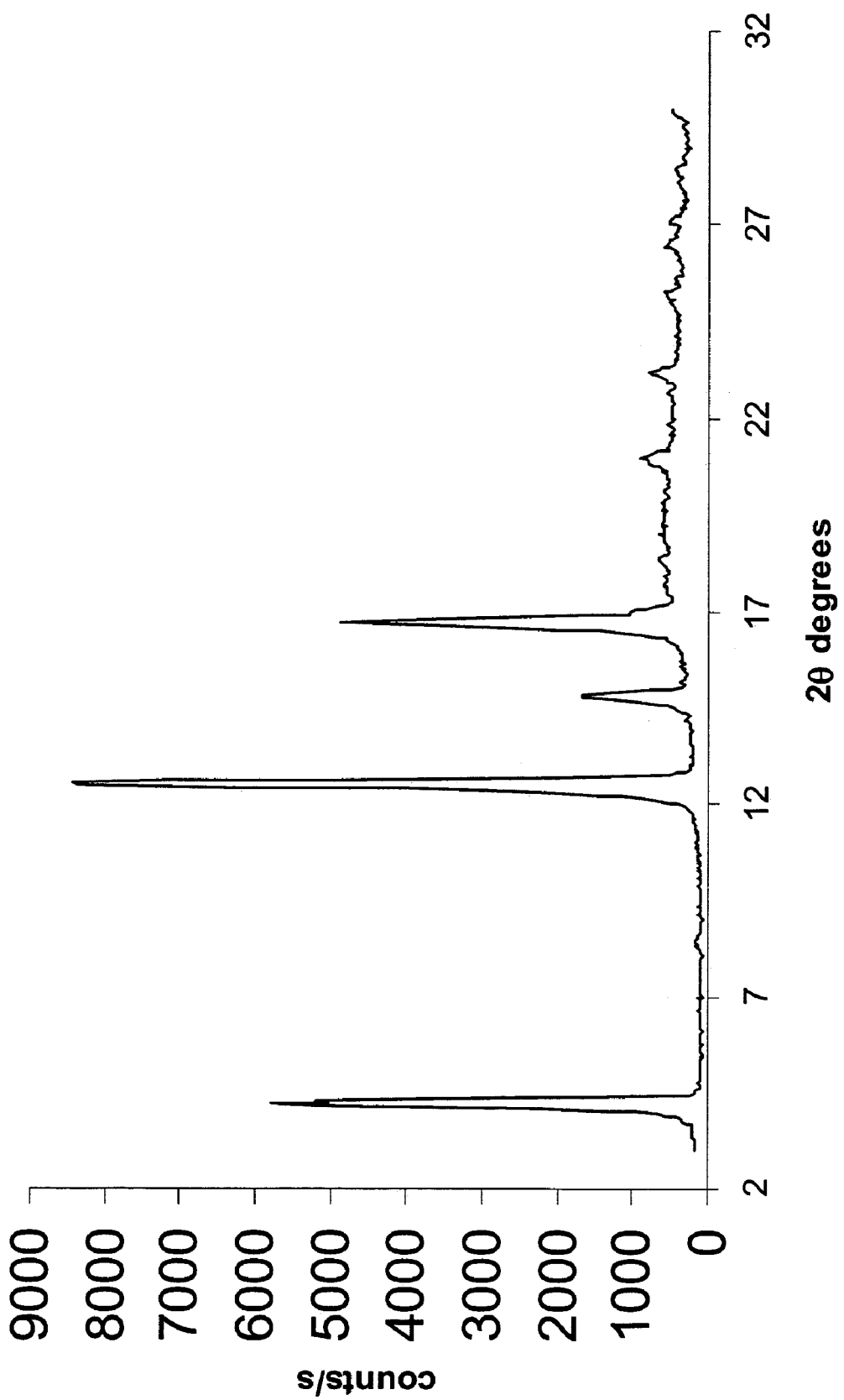
FIG. 8 presents an X-ray powder diffractogram of Temozolomide Form IV.

The X-ray powder diffractogram of the product is presented in FIG. 8 and reflections thereof listed in Table 4 above. The IR spectrum of the product is presented in FIG. 9.

Example 11

Preparation of Temozolomide Form V

In a 100 ml three necked round bottom flask equipped with a reflux condenser, a thermometer and a magnetic stirrer, Temozolomide (1 gram) was dissolved in 20 ml of ethylene glycol. The solution was heated using an oil bath to 100° C., and then left to cool to room temperature. The resulting crystals (0.7 gram) were filtered and dried in vacuum at 30° C. The X-ray powder diffractogram of the product is presented in FIG. 10 and reflections thereof listed in Table 5 above. The IR spectrum of the product is presented in FIG. 11.

Example 12

Preparation of Temozolomide Form VI

In a 100 ml three necked round bottom flask equipped with a reflux condenser, a thermometer and a magnetic stirrer, Temozolomide (1.5 gram) was dissolved in 140 ml of nitroethane. The solution was heated using an oil bath to 100° C., and then left to cool to room temperature. The resulting crystals (0.75 gram) were filtered and dried in vacuum at 30° C. The X-ray powder diffractogram of the product is presented in FIG. 12 and reflections thereof listed in Table 6 above. The IR spectrum of the product is presented in FIG. 13. The differential scanning calorimetry curve of the product is presented in FIG. 14.

Example 13

Preparation of Temozolomide Form VII

In a 100 ml three necked round bottom flask equipped with a reflux condenser, a thermometer and a magnetic stirrer, Temozolomide (1 gram) was dissolved in 16 ml of dimethylsulfoxide (DMSO). The solution was heated using an oil bath to 80° C., and then cooled inside ice. The resulting crystals (0.6 gram) were filtered and dried in vacuum at 30° C. The X-ray powder diffractogram of the product is presented in FIG. 15 and reflections thereof listed in Table 7 above. The IR spectrum of the product is presented in FIG. 16.

Example 14

Preparation of Temozolomide Form VIII

In a 100 ml three necked round bottom flask equipped with a reflux condenser, a thermometer and a magnetic stirrer, Temozolomide (1.5 gram) was dissolved in 500 ml of Acetone. The solution was heated using an oil bath to reflux, and then cooled in air. The resulting crystals (0.6 gram) were filtered and dried in vacuum at 30° C. The X-ray powder diffractogram of the product is presented in FIG. 17 and reflections thereof listed in Table 8 above. The IR spectrum of the product is presented in FIG. 18.

Example 15

Preparation of Temozolomide Form IX 1 gram of Temozolomide Form VI were heated inside a laboratory oven at 120° C. during 15 minutes. The X-ray powder diffractogram of the product is presented in FIG. 9 and reflections thereof listed in Table 2 above. The IR spectrum of the product is presented in FIG. 19. The differential scanning calorimetry curve of the product is presented in FIG. 20.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, the present invention is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. Crystalline Temozolomide Form III comprising at least one of the characteristics selected from the group consisting of:

a powder X-ray diffraction pattern exhibiting peaks at diffraction angles 2θ of about 10.8, 13.2, 14.7, 16.2, 16.8, 18, 19.1, 19.6, 21.5, 26.6, 23.8, 28.8, 29.8±0.2°; and an infrared spectrum with $v_{max}$ at about 1678, 731 and 712±4 cm$^{-1}$.

Figure 6:
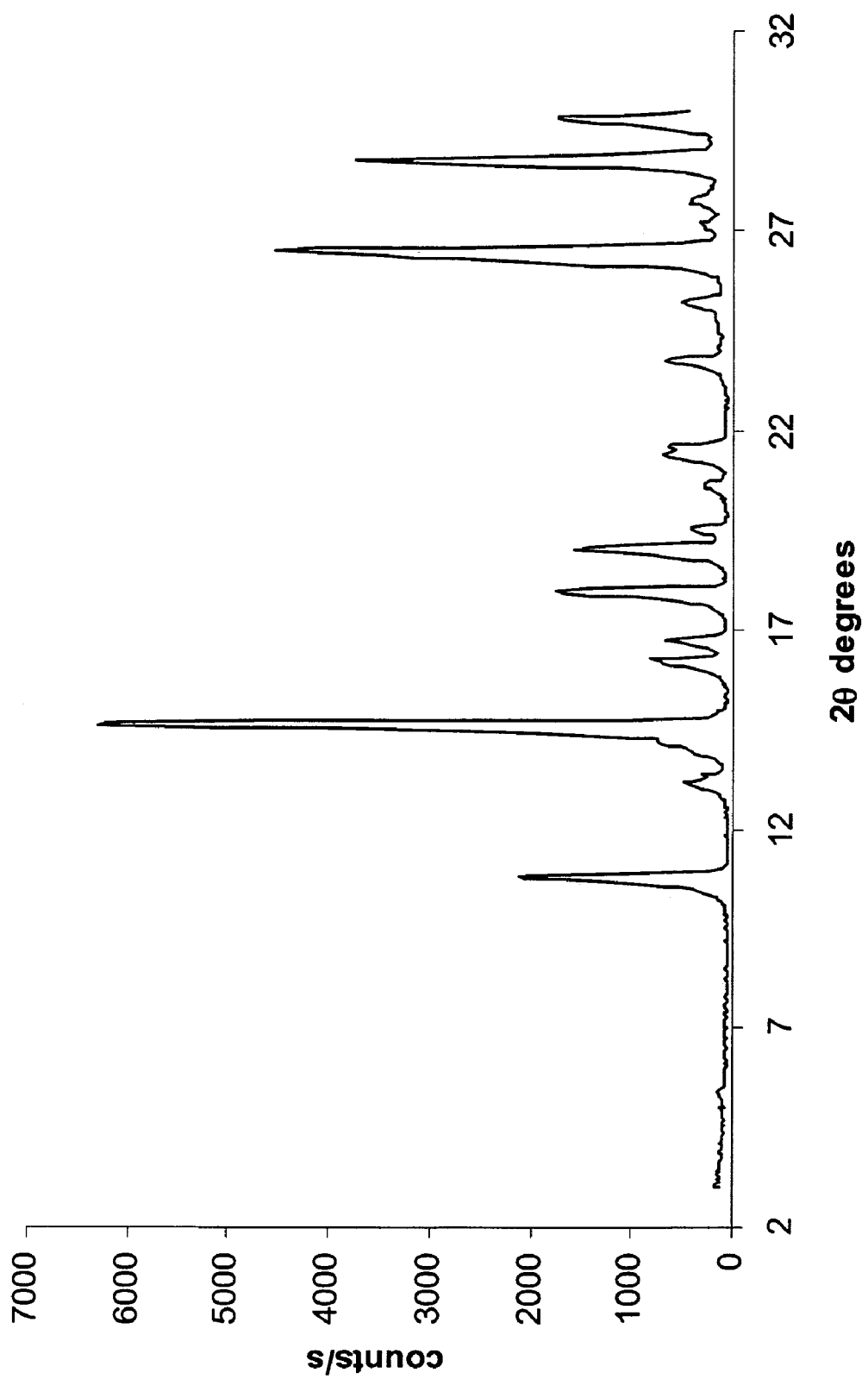
FIG. 6 presents an X-ray powder diffractogram of Temozolomide Form III.

2. The crystalline Temozolomide of claim 1, wherein said powder X-ray diffraction pattern is substantially as depicted in FIG. 6.

3. The crystalline Temozolomide of claim 1, wherein said infrared spectrum is substantially as depicted in FIG. 7.

4. A process of preparing crystalline Temozolomide Form III, the process comprising:

contacting Temozolomide with a solvent, said solvent including at least one solvent component selected from the group consisting of dimethylformamide, ethanol, and a mixture of benzyl alcohol and isopropanol, to thereby form a Temozolomide solution;

crystallizing said Temozolomide in said solution, to thereby obtain the crystalline Temozolomide Form III; and isolating the crystalline Temozolomide Form III.

5. A process of preparing crystalline Temozolomide Form III, the process comprising heating crystalline Temozolomide Form II to a transubstantiation temperature of about 120° C., to thereby obtain the crystalline Temozolomide Form III, wherein the Form II precursor exhibits a powder X-ray diffraction pattern with peaks at diffraction angles 2θ of about 10.8, 11.3, 14.5, 16.0, 17.9 and 19.1±0.2° or exhibits an infrared spectrum with $v_{max}$ at about 3451, 1749 and 1736±4 cm$^{-1}$, and the Form III product exhibits a powder X-ray diffraction pattern with peaks at diffraction angles 2θ of about 10.8, 13.2, 14.7, 16.2, 16.8, 18, 19.1, 19.6, 21.5, 26.6, 23.8, 28.8, 29.8±0.2° or exhibits an infrared spectrum with $v_{max}$ at about 1678, 731 and 712±4 cm$^{-1}$.

* * * * *